US012649904B2

(12) United States Patent
Lee et al.

(10) Patent No.: US 12,649,904 B2
(45) Date of Patent: \*Jun. 9, 2026

(54) METHOD FOR PREPARING COMPOSITION FOR CULTURING LUNG ORGANOIDS, COMPOSITION THEREFOR, AND ORGANOID CULTURE METHOD USING SAME

(71) Applicants: GRADIANT BIOCONVERGENCE CORPORATION, Seoul (KR); POSTECH RESEARCH AND BUSINESS DEVELOPMENT FOUNDATION, Pohang-si (KR)

(72) Inventors: Ha Ram Lee, Seoul (KR); Jin Ah Jang, Pohang-si (KR); Yoo Mi Choi, Pohang-si (KR); Dong Gyu Hwang, Pohang-si (KR); Myung Ji Kim, Daegu (KR)

(73) Assignees: GRADIANT BIOCONVERGENCE CORPORATION, Seoul (KR); POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 649 days.

This patent is subject to a terminal disclaimer.

(21) Appl. No.: 18/012,958

(22) PCT Filed: Jun. 24, 2021

(86) PCT No.: PCT/KR2021/007930
§ 371 (c)(1),
(2) Date: Dec. 26, 2022

(87) PCT Pub. No.: WO2022/005098
PCT Pub. Date: Jan. 6, 2022

(65) Prior Publication Data
US 2023/0287354 A1    Sep. 14, 2023

(30) Foreign Application Priority Data

Jun. 30, 2020    (KR) ........................ 10-2020-0080518
Apr. 30, 2021    (KR) ........................ 10-2021-0056942

(51) Int. Cl.
*C12N 5/071*        (2010.01)

(52) U.S. Cl.
CPC ........ *C12N 5/0688* (2013.01); *C12N 2513/00* (2013.01); *C12N 2533/90* (2013.01)

(58) Field of Classification Search
None
See application file for complete search history.

(56) References Cited

U.S. PATENT DOCUMENTS

2017/0275592 A1*    9/2017    Sachs ................. G01N 33/5011
2018/0126037 A1*    5/2018    Huh ................... A61L 27/3633
(Continued)

FOREIGN PATENT DOCUMENTS

KR    10-2011-0086176 A    7/2011
KR    10-2017-0078460 A    7/2017
(Continued)

OTHER PUBLICATIONS

Miller et al., Nature Protocols, 14:518-540 (2019) (Year: 2019).*
(Continued)

*Primary Examiner* — Thomas J. Visone
(74) *Attorney, Agent, or Firm* — Goldilocks ZONE IP LAW

(57)        ABSTRACT

The present invention relates to a preparation method of a composition for culturing lung organoids, a composition thereby, and an organoid culture method using the same. The present invention is capable of creating an environment that is more similar to an actual tissue than a conventional MATRIGEL®-based culture system, and in particular, exhibits an effect of facilitating tissue differentiation in lung (Continued)

Porcine lung    Decellularization    Decellularization support    Organoid culture Patient-specific organoids Drug screening organoid culture and effectively developing into a form that is similar to an actual tissue.

4 Claims, 23 Drawing Sheets
(21 of 23 Drawing Sheet(s) Filed in Color)

(56)                    References Cited

U.S. PATENT DOCUMENTS

2019/0201586 A1*    7/2019   Li ........................... A61L 27/56
2020/0093959 A1*    3/2020   Snoeck ............... C12N 5/0688

FOREIGN PATENT DOCUMENTS

KR          10-2015368  B1       8/2019
KR      10-2019-0143703  A      12/2019
KR      10-2019-0143830  A      12/2019
KR      10-2020-0025502  A       3/2020

OTHER PUBLICATIONS

Pouliot et al., Tiss. Eng. C, 26:332-333-346 (2020) (Year: 2020).*
Hilster et al., Am. J. Physiol. Lung Cell Mol. Physiol., 318:L698-L704 (2020) (Year: 2020).*
Pouliot et al., J. Biomed. Mater. Res. A, 104A:1922-1935 (2016) (Year: 2016).*
Jenna L. Balestrini, et al., Comparative Biology of Decellularized Lung Matrix: Implications of Species Mismatch in Regenerative Medicine, Biomaterials. Sep. 2016, pp. 220-230, vol. 102, HHS Public Access.

* cited by examiner

| | | dsDNA (µg/g) | GAGs (µg/g) | Collagen (µg/g) |
|---|---|---|---|---|
| Lung | Native | 17.32 ± 1.31 | 31.87 ± 1.73 | 1.89 ± 0.10 |
| | dECM | 0.70 ± 0.06 | 30.15 ± 0.54 | 6.03 ± 0.27 |

Matrigel

LudECM

FIG. 9b

Lung cancer organoid (cystic type)

FIG. 11

Lung cancer organoid (solid type)

Lung cancer organoid (cystic type)

FIG. 15

Proliferation

METHOD FOR PREPARING COMPOSITION FOR CULTURING LUNG ORGANOIDS, COMPOSITION THEREFOR, AND ORGANOID CULTURE METHOD USING SAME

CROSS-REFERENCE TO RELATED APPLICATIONS

This application claims the benefit under 35 U.S.C. section 371, of PCT International Application No. PCT/KR2021/007930, filed on Jun. 21, 2021, which claims priority to Korean Patent Application No. 10-2020-0080518, filed on Jun. 30, 2020, and Korean Patent Application No. 10-2021-0056942, filed on Apr. 30, 2021, in the Korean Intellectual Property Office, both of which are hereby incorporated by reference in their entireties.

TECHNICAL FIELD

The present invention relates to a preparation method of a composition for culturing lung organoids, a composition thereby, and an organoid culture method using the same.

BACKGROUND ART

Organoids are three-dimensional cell aggregates formed from stem cells through phylogeny and differentiation, and they allow for the observation of the development process of organs and the reproduction of actual tissues in terms of function and structure. As such, a support or scaffold, which plays a supporting role so that cells can be attached and grow, also plays a very important role in biological tissue engineering, and it also plays an important role in the growth of cells seeded in a porous structure and cells migrating from the surroundings of the tissue. Most of the cells in the human body are adherent cells that are attached to grow, and if there is no place to be attached to, the cells cannot grow and eventually die. Therefore, the scaffold should provide a compatible environment for cell adhesion, differentiation, growth and cell migration. Such a scaffold can be made of various materials, and research to develop a scaffold by using a natural material, a synthetic polymer, bioceramics, and a polymer-ceramic composite material is being actively conducted. Accordingly, organoids that mimic various organs have been developed so far, and these are mainly MATRIGEL® cultured in MATRIGEL®, a three-dimensional culture environment.

However, although MATRIGEL® is widely used for organoid culture, it is derived from mouse sarcoma, and there is no particular substitute. Therefore, despite the high cost, there is no choice but to rely on MATRIGEL®. In addition, certain components are dominating in MATRIGEL® and there is a limitation in reflecting the tissue-specific characteristics. To complement and replace this, decellularization of tissues and organs has been studied as a promising method for preparing functional scaffolds for cell culture and transplantation, and there is an emerging need for the method. However, the organoids produced by the current organoid culture technology have many differences from the actual human tissues in terms of the degree of differentiation and functions, and thus the development of a technology for culturing more mature organoids is required.

In this regard, Non-Patent Document 1 below teaches that a decellularized lung tissue scaffold can be used for lung tissue regeneration. However, the decellularization process is not specifically disclosed therein.

In particular, the whole lung was decellularized in a number of previous studies, but in the present invention, decellularization was performed by separating the bronchus and micro-bronchus and using the alveoli only (see Example 1 of the present invention, including the details about removing the bronchus and micro-bronchus during the lung arrangement). Even if a conventional decellularization process is employed, there is a difference in the content of residual DNA, GAGs, and collagen. In particular, in the present invention, decellularization conditions were established such that a large amount of collagen VI, laminin, and fibronectin components can remain (see Example 8).

In addition, the Patent Document 1 below discloses a preparation method of a brain organoid culture composition in which brain tissue is decellularized and lyophilized, the lyophilized tissue is dispersed and then solutionized in an acidic solution, and the pH is adjusted. However, this is for brain tissue and not for the lung. Moreover, it is only described about the solutionizing that pepsin or trypsin can be used as an acidic solution, and just the general gelation temperature (25 to 38° C.) after pH adjustment is described.

Therefore, there always exists a need for research and development on a preparation method of a composition for culturing lung organoids, which can increase the culture efficiency of lung organoids, and a composition thereby and a organoid culture method using the same.

PRIOR ARTS

Patent Document (Patent Document 1) KR patent publication: 10-2019-0143830 (published on Dec. 31, 2019)
(Patent Document 2) KR registered patent: 10-2015368
(Patent Document 3) KR patent publication: 10-2017-0078460

Non-Patent Document (Non-Patent Document 1) Balestrini, J L. et al" Biomaterials (2016) 102:220-230

DETAILED DESCRIPTION OF THE INVENTION

Technical Problem

The purpose of the present invention is to solve the problem that the MATRIGEL®-based culture system, which is an extract derived from animal cancer tissue, has a large difference between batches, is incapable of simulating the environment of the actual tissue, and has an insufficient efficiency of tissue differentiation and development. The composition of the present invention is to provide an optimal environment for organoid culture by creating an actual tissue-like environment and to improve organ-specific differentiation potency.

In addition, another purpose of the present invention is to provide a composition for culturing an organoid, which has excellent physical properties of a decellularized tissue and which can also significantly increase the organoid culture efficiency, and a preparation method of the same.

In addition, another purpose of the present invention is to provide a composition for culturing an organoid that is capable of providing excellent physical properties of a decellularized tissue, preventing gelation, and enabling uniform hydrogelation, and a preparation method of the same.

Technical Solution

In order to achieve the purposes above, the present invention provides a preparation method of a composition for culturing lung organoids, the composition thereby, and a organoid culture method using the same.

The present invention provides a preparation method of a composition for culturing lung organoids, the method comprising: S1) decellularizing lung tissue; S2) lyophilizing the decellularized tissue; S3) pulverizing the lyophilized tissue; S4) lysing the pulverized tissue by adding a proteopeptic enzyme and an acid; and S5) adjusting the pH by adding a basic solution to the lysate.

Since the decellularized tissue contains an actual tissue-specific extracellular matrix component, it is able to provide a physical, mechanical, and biochemical environment of the tissue, and is very efficient in promoting the differentiation into lung tissue cells and their tissue-specific functionality.

The "organoid" refers to a micro-sized biological organ produced in the form of an artificial organ by culturing cells derived from tissues or pluripotent stem cells in a 3D form.

The organoids are three-dimensional tissue analogues including organ-specific cells that are developed from stem cells and that self-organize in a manner that is similar to the in vivo state, and they can develop into specific tissues by patterning limited factors (for example, growth factors).

The organoid has the intrinsic physiological properties of the cell and may have an anatomical structure that mimics the original state of a cell mixture (including not only limited cell types but also residual stem cells and proximal physiological niche). Through a three-dimensional culture method, the organoid may have a shape and a tissue-specific function, such as that of an organ in which cells and cellular functions are better arranged and which has functionality.

According to one embodiment of the present invention, the S1) decellularizing may comprise, twice or more, a process of adding at least one solution selected from sodium dodecyl sulfate (SDS), polyethylene glycol (PEG), TRITON® X-100, ethylenediaminetetraacetic acid (EDTA), peracetic acid, deoxycholic acid, 3-[(3-cholamidopropyl) dimethylammonio]-1-propanesulfonate (CHAPS), sodium deoxycholate, ammonium hydroxide, trypsin, benzonase, DNase, calcium chloride, magnesium sulfate, sodium azide ($NaN_3$) and sodium chloride. In addition, S1) may comprise a washing process in the middle of the two decellularization processes. In one embodiment, the tissue may be stirred during the decellularization.

Decellularized extracellular matrix (dECM) can be obtained through the method described above, and the "dECM" means a natural scaffold for cell growth prepared through decellularization of tissues found in mammals and multicellular organisms. The extracellular matrix may be collagen, elastin, laminins, glycosaminoglycans, proteoglycans, antimicrobials, chemoattractants, cytokines, and a mixture of structural and non-structural biomolecules that are not limited by growth factors. The extracellular matrix contain about 90% collagen in various forms in mammals. Extracellular matrixes derived from various biological tissues may have different overall structures and compositions due to the unique role required for each tissue.

According to one embodiment of the present invention, the decellularizing may comprise: a1) washing a lung tissue; a2) treating with at least one selected from peracetic acid, TRITON®-X, sodium dodecyl sulfate and sodium chloride;

a3) washing; a4) treating with at least one selected from peracetic acid, TRITON®-X, sodium dodecyl sulfate and sodium chloride; a5) washing; a6) treating with at least one selected from peracetic acid, TRITON®-X, sodium dodecyl sulfate and sodium chloride; and a7) washing.

More specifically, the decellularizing may comprise: a1) washing a lung tissue; a2) treating with at least one selected from peracetic acid, TRITON®-X, sodium dodecyl sulfate and sodium chloride; a3) washing; a4) treating with at least one selected from peracetic acid, TRITON®-X, sodium dodecyl sulfate and sodium chloride; a5) washing; a6) treating with at least one selected from peracetic acid, TRITON®-X, sodium dodecyl sulfate and sodium chloride; and a7) washing.

In addition, the washing of a1), a3), a5), or a7) may be performed with at least one selected from distilled water, physiological saline, and phosphate buffered saline. When decellularizing is performed by the method described above, a composition for culturing organoids having excellent differentiation into tissue cells and having excellent tissue specificity can be obtained. In particular, a composition capable of maintaining the mutational properties of lung cancer organoids may be obtained in the lung dECM scaffold using the same.

According to one embodiment of the present invention, a1) may be performed for 3 to 48 hours, a2) for 12 to 120 hours, a3) for 6 to 24 hours, a4) for 0.5 to 4 hours, a5) for 6 to 48 hours, a6) for 0.5 to 4 hours, and a7) for 1 to 6 hours. Specifically, a1) may be performed for 3 to 24 hours, a2) for 24 to 48 hours, a3) for 9 to 18 hours, a4) for 1 to 3 hours, a5) for 12 to 36 hours, a6) for 1 to 3 hours, and a7) for 2 to 4 hours. When the steps are performed in the ranges described above, a composition for culturing organoids having excellent differentiation into tissue cells and having excellent tissue specificity can be obtained.

According to one embodiment t of the present invention, the S2) lyophilizing is for lyophilizing a tissue decellularized in S1). The lyophilizing methods or specific conditions are not particularly limited, and various methods or conditions known in the art may be used. For example, the decellularized tissue may be frozen at −100° C. to −50° C., and then dried at −70° C. to −30° C. for 1 to 10 days.

According to one embodiment of the present invention, the S3) pulverizing is for pulverizing the tissue lyophilized in S2). The pulverizing methods or sizes, and specific conditions are not particularly limited, and various methods or sizes and conditions known in the art may be used. For example, the lyophilized tissue may be put into a mortar and pulverized by using liquid nitrogen.

According to one embodiment of the present invention, the S4) lysing is for lysing the tissue pulverized in S3) above. In other words, the pulverized tissue can be lysed by adding a proteopeptic enzyme and an acid to the same, and stirring the resulting mixture.

Here, the present invention is characterized in that a proteopeptic enzyme and an acid are added to the pulverized tissue to lysate by stirring the resulting mixture at a speed of 330 rpm to 500 rpm for 72 to 96 hours. Preferably, the resulting mixture may be lysed by stirring at a speed of 330 rpm for 72 to 96 hours. In addition, the resulting mixture may be lysed by stirring at a speed of 330 rpm to 500 rpm for 96 hours. More preferably, the resulting mixture may be lysed by stirring at a speed of 330 rpm for 96 hours.

The inventors found that not in the process of decellularization but in the process of adding a proteopeptic enzyme and an acid to the decellularized, lyophilized and pulverized dECM and lysing the resulting mixture, the stirring time and speed are important to the physical properties and the subsequent culture effects of the decellularized tissue, and then completed the present invention.

As shown in the Examples to be described later, it was confirmed that when the decellularized tissue was lysed while stirring at a speed of 330 rpm to 500 rpm for 72 hours to 96 hours in the lysing, excellent rheological properties (physical properties) and culture effects were obtained, compared to the cases where the lysing was performed differently.

In other words, the modulus values representing the physical properties for each stirring time were found to be in the order of 24 h<72 h≒96 h>120 h. In other words, it was confirmed that the physical properties were best when the stirring time was 72-96 hours. In addition, although the physical properties continued to increase when the stirring time was 120 hours, the experiment was difficult because many bubbles were generated when the organoid is encapsulated. In particular, death of many organoids was found in the dECM stirred for 24 hours and 120 hours, indicating that the properties are important in the culture of an organoid. In addition, the culture tendency in the organoid culture was improved in the order of 24 h<72 h≒96 h>120 h (120 h<72 h).

In addition, the modulus values representing the physical properties for each stirring speed were found to be in the order of 80<150<330≤500>800>1000 (80<1000<150<800<330<500) rpm, and the best physical properties were found at 330-500 rpm. In addition, it was found that the culture efficiency in the organoid culture was in the order of 80=250«330≒500»1000 (80≒250≒1000«330≒500) and that the dome formation was impossible at 80 rpm. In particular, death of many organoids was found with no living organoids observed in the dECM stirred at 80, 250, and 1000 rpm, indicating that the properties are important in the culture of an organoid, and compatible conditions could be set accordingly.

According to one embodiment of the present invention, the proteopeptic enzyme in S4) may be pepsin or trypsin. Preferably, it may be pepsin.

According to one embodiment of the present invention, the acid in S4) may be hydrochloric acid or acetic acid. Preferably, it may be acetic acid.

According to one embodiment of the present invention, the S5) adjusting the pH is for adjusting the pH by adding a basic solution to the lysate in S4) above. The method of adding a basic solution or the type of the basic solution to be used is not particularly limited, and various basic solutions known in the art may be used. The final pH can be adjusted to be 7 to 7.5.

Here, the present invention s particularly characterized in that the S5) adjusting the pH is performed within a range of 1° C. to 10° C. in order to prevent gelation. Preferably, it may be performed within a range of 2° C. to 7° C. In other words, the pH adjusting process may not be performed at room temperature, but may be performed in a lower refrigeration temperature range.

In addition, the S5) adjusting the pH may be performed on ice in order to prevent gelation. The expression of performing "on ice" means that the lysate is present on the surface of the ice or provided in the ice. For example, the pH may be adjusted by adding a base, after inserting the container containing the lysate into ice.

The present inventors found that not in the process of decellularization but in the process of adjusting the pH by adding a basic solution to the decellularization lysate, the temperature (1° C. to 10° C.) and/or conditions (on ice)

affect the hydrogelation of the composition and the subsequent encapsulation of organoids, and then completed the present invention.

As shown in Examples to be described later, when the process of adjusting pH by adding a basic solution to the decellularized lysate is performed "on ice (at 1° C. to 10° C.)," the gelation of the lysate may be prevented, and uniform hydrogelation may be possible. In addition, it was confirmed that the lung dECM scaffold prepared in this way has excellent rheological properties (physical properties) and culture effects, compared to the case where the lung dECM scaffold was prepared differently.

In other words, it was confirmed that the decellularization composition of which pH was adjusted on ice according to the present invention was able to form a uniform gel during the gelation process, but the decellularization composition of which pH was adjusted at room temperature (RT) underwent partial gelation and aggregation and so the dome shape was not maintained but broken and the physical properties thereof (complex modulus (G*)) were also low.

As described above, the present invention may be characterized in that the pH adjustment process is not performed at room temperature but in a lower refrigeration temperature range, and further, the basic solution is stored at a refrigeration temperature within a range of 1° C. to 10° C. in advance before use. A basic solution stored at a refrigeration temperature may preferably be used because the gelation prevention and uniform hydrogelation may be performed better.

According to one embodiment of the present invention, by the present invention described above, 95% or more of tissue cells, specifically 97% or more of the tissue cells can be removed, compared to the tissue cells before the treatment. In addition, the glucosaminoglycane content may be 90% to 120%, specifically 95% to 110%, compared to the glucosaminoglycane content before the treatment. In addition, the collagen content may be 200% to 2000%, specifically 500% to 1700%, compared to the collagen content before the treatment. Through this, an excellent cell removal rate may be obtained, and the useful components can be retained so that a scaffold based on the retained useful components may be used to obtain an organoid culture composition in which the organoid culture is performed well (culture, expansion, proliferation) and which has excellent differentiation into tissue cells and excellent tissue specificity.

According to one embodiment of the present invention, a cytokine-rich composition that is excellent for organoid culture may be obtained through the method described above. Specifically, compared to MATRIGEL®, at least one cytokine selected from angiopoietin-1, insulin growth factor, TGF-beta, and placental growth factor may have been increased. Through this, an organoid culture composition in which the organoid culture is performed well (culture, expansion, proliferation) and which has excellent differentiation into tissue cells and excellent tissue specificity may be obtained.

The present invention also provides a composition for culturing lung organoids prepared by the method described above.

According to one embodiment of the present invention, the composition may contain 0.1% to 10% (w/v) of dried decellularization tissue based on the total volume of the composition, specifically, 0.1% to 5% (w/v). In the case where the content described above is satisfied, when an organoid is cultured in the decellularization scaffold (dECM) based on the present invention, an excellent organoid culture composition in which the organoid culture is performed well (culture, expansion, proliferation) and in particular, which improves the organoid differentiation potency in the lung dECM and well retains the mutation properties of a lung cancer organoid may be obtained.

According to one embodiment of the present invention, the composition of the present invention may further include MATRIGEL®.

The "MATRIGEL®" is a protein complex extracted from EHS (Engelbreth-Holm-Swarm) mouse sarcoma cells (name of product manufactured by BD Bioscience) and may comprise an extracellular matrix, such as laminin, collagen and heparan sulfate proteoglycan, and fibroblast growth factor (FGF), epidermal growth factor (EGF), insulin-like growth factor (IGF), TGF-β or platelet-derived growth factor (PDGF).

According to one embodiment of the present invention, the composition may contain 0.1% to 10% (w/v) of dried decellularization tissue based on the total volume of the composition, specifically 0.1 to 5% (w/v). In the case where the content described above is satisfied, when an organoid is cultured in the decellularization scaffold (dECM) based on the present invention, an excellent organoid culture composition in which the organoid culture is performed well (culture, expansion, proliferation) and in particular, which improves the organoid differentiation potency in the dECM and well retains the mutation properties of a lung cancer organoid may be obtained.

The present invention also provides a lung organoid culture method comprising: culturing a lung organoid in the composition for culturing lung organoids described above.

The culture refers to a process of maintaining and growing cells under compatible conditions, and compatible conditions may mean, for example, the temperature at which the cells are maintained, nutrient availability, atmospheric $CO_2$ content, and cell density.

Compatible culture conditions for maintaining, proliferating, expanding and differentiating different types of cells are known and documented in the art. The compatible conditions for the formation of the organoid may be conditions that facilitate or allow cell differentiation and formation of multicellular structures.

The present invention also provides a lung organoid culture method for culturing a lung organoid, the method comprising: culturing a lung organoid in the composition for culturing lung organoids described above.

The present invention also provides an extracellular matrix scaffold for culturing organoids prepared from the composition for culturing lung organoids described above.

The present invention also provides a lung organoid culture method comprising: mixing the extracellular matrix support for culturing organoids and the lung organoid.

The details of other Examples are included in the detailed description and drawings.

Advantageous Effects

The present invention is capable of creating an environment that is more similar to an actual tissue than a conventional MATRIGEL®-based culture system, and in particular, exhibits an effect of facilitating tissue differentiation in lung organoid culture and effectively developing into a form that is similar to an actual tissue. In addition, the present invention exhibits effectiveness by maintaining genetic mutations even in tumor-derived organoid culture.

In addition, when the decellularized tissue is stirred for a specific time and/or at a specific rpm in lysing the decellularized tissue with a proteopeptic enzyme and an acid according to the present invention, the physical properties of the decellularized tissue become excellent and the organoid culture rate is significantly increased.

In addition, when the process of adjusting the pH by adding a basic solution to the decellularization solution according to the present invention is performed under specific conditions, the physical properties of the decellularized tissue become excellent, gelation can be prevented, and uniform hydrogelation can be achieved.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 8a shows the results of sol-gel transition or gelation kinetics obtained by preparing the lung dECM according to an Example of the present invention at 2% and 1% and then analyzing the dECM alone and the mixtures prepared by mixing with MATRIGEL® according to the presented ratios.

FIGS. 9a and 9b show an analysis of the cytotoxicity of the lung tumor organoids using a Live/Dead assay according to an Example of the present invention. Among the human-derived lung tumor organoids that were cultured based on the lung 1% dECM prepared according to an Example of the present invention and under the conditions of using the dECM alone and mixing with MATRIGEL® according to the presented ratios, FIG. 9a shows the results of the culture and the toxicity analysis of the solid type and FIG. 9b shows those of the cystic type.

FIG. 11 shows the sequencing results the human-derived lung tumor organoids according to an Example of the present invention, verifying the culture effectiveness of the lung tumor organoids cultured in dECM.

FIG. 12 shows the results of performing long-term culture of the human-derived lung tumor organoids cultured in the dECM according to an Example of the present invention, confirming the possibility of long-term culture of the lung tumor organoids cultured in the dECM. Among the human-derived lung tumor organoids that were cultured based on the lung 1% dECM prepared according to an Example of the present invention and under the conditions of using the dECM alone and mixing with MATRIGEL® according to the presented ratios, FIG. 12a shows the results of analyzing the cytotoxicity of the organoids on Day 17, Day 30 and Day 44 during the culture of the solid type for 48 days.

FIG. 15 is a photograph showing the state of culturing the lung organoids for each stirring time in the S4) lysing according to an Example of the present invention.

BEST MODE

Figures 1, 2:
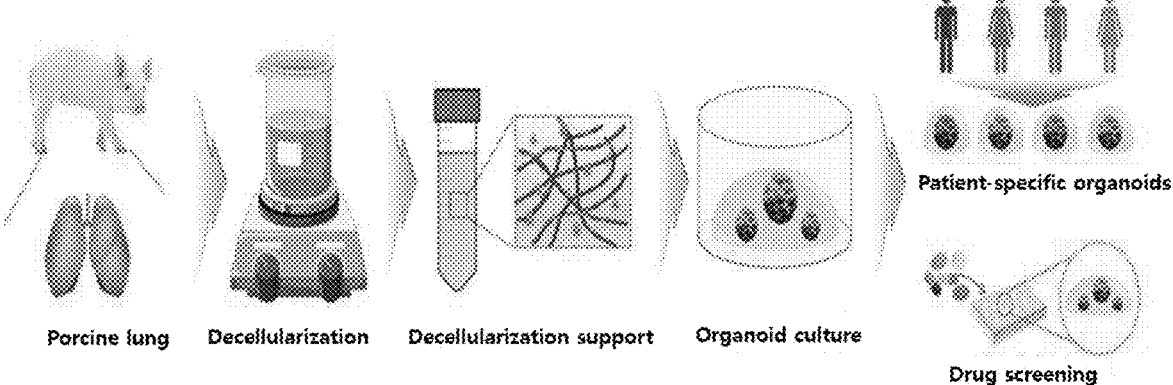
FIG. 1 shows a representative diagram of preparing a composition for culturing lung organoids according to an embodiment of the present invention, and the organoid culture and application using the composition thereby.
FIG. 2 shows an analysis of dsDNA, GAGs, and collagen contents compared to the native tissues of lung dECM according to an Example of the present invention.

Since various transformations can be applied to the present invention, and the present invention can have various Examples, specific Examples are illustrated in the drawings and described in detail in the detailed description. However, this is not intended to limit the present invention to specific embodiments, and should be understood to include all transformations, equivalents, and substitutes included in the principles and scope of the present invention. In describing the present invention, if a specific description of a related known technology may obscure the gist of the present invention, the detailed description thereof will be omitted.

The terms used in the present application are only used to describe specific embodiments, and are not intended to limit the present invention. The singular expression includes the plural expression unless the context clearly dictates otherwise. In the present application, terms such as "comprise" or "have" are intended to designate that a feature, number, step, operation, component, part, or combination thereof described in the specification exists, but one or more other features It should be understood that this does not preclude the existence or addition of numbers, steps, operations, components, parts, or combinations thereof.

Terms such as first, second, etc. may be used to describe various features, but the features should not be limited by the terms. The above terms are used only for the purpose of distinguishing one feature from another feature.

Example 1: Decellularization of Porcine Lungs (1) Lung Tissue Trimming and Slicing After removing the bronchus and micro-bronchus out of the lung tissue, the trimmed lung tissue is frozen at −80° C. for 24 hours. (Store at −80° C. until use) After slicing the frozen lung tissue to a thickness of 1-2 mm, and the sliced lung tissue is moved to a beaker. In order to prevent contamination of the tissue and evaporation of the solution, the entrance of the beaker must be covered with aluminum foil.

(2) Decellularization Reagent Treatment

Before the reagent treatment, the tissue is washed with distilled water (dH$_2$O; secondary water) for 3 hours until almost no blood comes out. The tissue is cut into small pieces by using scissors to remove the remaining micro-bronchus. In this step, the amount of the tissue is reduced. After washing the tissue, 1% SDS is treated within 24 hours. Washing is performed with distilled water for 12 hours to remove the remaining SDS. The tissue is treated with 1 M sodium chloride (NaCl) for 2 hours. Washing is performed with distilled water for 24 hours to remove residual reagents. For sterilization, ethanol containing peracetic acid is treated for 2 hours. Hereinafter, tertiary distilled water (ddH$_2$O) is used as all base buffers. After washing with tertiary distilled water (ddH$_2$O) for 2 hours, washing is performed with 1×PBS for 1 hour. The tissue is moved to a 50 mL conical tube by using forceps. After freezing the tissue at −80° C., the tissue is lyophilized at −50° C. for 4 days. In the entire decellularization process, the washing process employs a stirrer at a speed of 100-150 rpm. In each of the other reagent processing steps, the stirring speed is kept within 100 rpm to ensure that the tissue and the reagent can react sufficiently. In all steps, forceps and scissors are used to loosen the tissue in order to prevent congelation of the tissue. In addition, the beaker and the magnetic bar are washed with distilled water in each step in order to remove the remaining reagent.

Example 2: Preparation of Lung dECM Scaffolds

The lyophilized lung dECM prepared in Example 1 is pulverized with liquid nitrogen by using a mortar and a pestle. The lung dECM is put into a 50 mL conical tube and lysed in 0.5 M acetic acid with pepsin for 96 hours. A cell strainer is used to filter the lung dECM powder that is not lysed. In order to prevent gelation, the steps hereinafter should be performed on ice. After adding cold 10×PBS before treating with 10 N sodium hydroxide (NaOH), the lung dECM is homogeneously mixed by using a vortex mixer. A pH indicator strip is used to observe the change of pH, and 10 N sodium hydroxide (NaOH) is added to adjust the final pH to 7-7.5. Cold 1×PBS is added to adjust to the final volume.

Example 3: Lung dECM Biochemical Assay

As the verification of the decellularized pig lung tissue, the contents of dsDNA, GAGs and collagen in the decellularized tissue is confirmed, compared to the native tissue.

(1) Confirmation of dsDNA Content in Decellularized Lung Tissue

GeneJET Genomic DNA Purification Kit was used to separate dsDNA from the native and decellularized tissues. The separation was carried out in the same manner as described in the manufacturer's protocol. The dsDNA content in the decellularized tissue compared to the native tissue was confirmed by using Quant-iT™ PicoGreen™ dsDNA Assay Kit. The assay was carried out in the same manner as described in the manufacturer's protocol.

(2) Preparation of Solution for Confirming the Content of Glucosaminoglycans (GAGs) and Collagen in Decellularized Lung Tissue A papain solution is prepared for the digestion of dECM. In the preparation of all solutions (papain, buffer, etc.), the amount of the solution can be adjusted according to the number of samples. The specific process is described below. ① 0.1 M sodium phosphate (monobasic), 0.5 mM Na2-EDTA, and 5 mM cysteine-hydrochloric acid are dissolved in autoclaved distilled water. ② The pH of the solution is adjusted to 6.5 by adding 10 N sodium hydroxide. ③ A papain stock prepared at 10 mg/mL is added to the solution above, and the resulting mixture is mixed well with a vortex mixer to be mixed homogeneously.

A solution for the dimethyl-methylene blue (DMMB) assay is prepared. The specific process is described below. ① To prepare a DMMB dye, 1,9-dimethyl-methylene blue zinc chloride double salt, glycine, and sodium chloride are dissolved in autoclaved distilled water. The pH is adjusted to 3 by adding 0.5 M HCl solution, while measuring the change of pH by using a bench-top pH meter. Then, after filtering by using a filter, an aliquot of the solution is taken in a conical tube, which is wrapped with aluminum foil and stored. ② A 10 mg/mL chondroitin sulfate A solution stock is prepared at 100 µg/mL by using 1×PBS.

A solution for the hydroxyproline assay is prepared. The specific process is described below. ① Chloramine Working Solution: Sodium acetate, citric acid, and sodium hydroxide are dissolved in distilled water, and glacial acetic acid, toluene, and IPA are added. The chloramine working solution is stored at 4° C. and can be used for about 6 months. ② Chloramine T solution: After dissolving Chloramine T in the chloramine working solution, IPA is added. The mixture is mixed well with a vortex mixer to be mixed homogeneously. However, the Chloramine T solution should be prepared immediately before use. ③ P-DAB solution: P-DAB is added to perchloric acid, IPA is added, and the mixture is mixed well. However, the P-DAB solution should also be prepared just before use and since it is sensitive to light, the tube should be wrapped with aluminum foil until use.

(3) dECM Digestion of Decellularized Lung Tissue

The lyophilized tissue is put into a 1.7 mL microcentrifuge tube (e-tube) to which the papain solution is added, and the resulting mixture is mixed well with a vortex mixer. The e-tube containing the tissue is inserted into rubber racks, which are floated on water added into a beaker, and then the tissue is digested at 60° C. for 16 hours. However, the tissue should be completely lysed without any remaining tissue. Centrifugation is performed at 12000×g for 20 minutes, and the supernatant is taken and transferred to a new e-tube.

(4) Confirmation of the Content of Glycosaminoglycans (GAGs) and Collagen in Decellularized Lung Tissue A DMMB assay is performed to quantify the GAGs in the dECM. The specific process is described below. ① A standard in a specific range according to the purpose of the experiment is prepared by using chondroitin sulfate A solution stock prepared at 100 µg/mL and distilled water. ② The standard and samples are loaded in triplicate into a 96-well plate at 40 µL/well. ③ The DMMB dye is added at 160 µL/well by using a multi-channel pipettor. ④ The absorbance is measured at a 525 nm wavelength with a microplate reader.

A hydroxyproline assay is performed to quantify the amount of collagen in the dECM. The specific process is described below. ① The tissue lysed in the papain solution and the same amount of hydrochloric acid are subject to a reaction in an oven at 120° C. for 16 hours. ② After the reaction, the residue remaining on the glass wall is dried and cooled at room temperature for 3 hours, and then lysed again in 1×PBS. ③ The completely lysed sample is transferred to an e-tube and centrifuged at 5,000×g for 10 minutes at 4° C., and only the supernatant is transferred to a new e-tube. ④ During the centrifugation, the 100 µg/mL hydroxyproline solution stock is diluted with distilled water to prepare a standard in a specific range according to the purpose of the experiment. ⑤ The standard and samples are loaded in triplicate into a 96-well plate at 50 µL/well. ⑥ The chloramine T solution in a volume of 50 µL is added, and then the resulting mixture is subject to a reaction at room temperature for 20 minutes. ⑦ The P-DAB solution in a volume of 50 µL is added and then the resulting mixture is subject to a reaction 60° C. for 30 minutes. Since P-DAB is sensitive to light, the loading should be conducted with the light off, and then the plate should be wrapped with aluminum foil to perform incubation. ⑧ After cooling for 30 minutes at room temperature, the absorbance is measured at a 540 nm with a microplate reader.

(5) Experiment Results

The specific experimental results are shown in FIG. 2.

In the case of the lung dECM, compared to the native group, the DNA content was 2.05%, and more than 97% of the cells were removed. In addition, the content of GAGs, of which loss occurs mainly in the decellularization process, was about 110% in the lung dECM, which was similar to that of the native group. Therefore, the decellularization process was considered as having been well established. The collagen content in the lung dECM was 573% compared to the native group, and so it was verified that cells were removed during the decellularization process and the main components s of the extracellular matrix were well preserved.

Example 4: Rheological Characterization of Lung dECM

(1) Experimental Method

The lung dECM scaffold is prepared at pH 7 to evaluate the rheological properties. The 20 mm cone plate geometry (cone diameter of 20 mm at a 2° angle) is set in the rate-controlled mode of a rheometer. An experiment sequence in the installed software program (TRIOS) is crated to measure the viscosity, gelation kinetics, and dynamic modulus of the dECM scaffold.

Gelation kinetics: The dECM scaffold is placed on a plate, and the complex modulus (G*) is calculated by measuring the storage & loss modulus of the dECM scaffold at 4-37° C. at an incremental increase rate (time-sweep mode) of 5° C./min.

Dynamic modulus: Before the measurement, the dECM scaffold is placed on the plate at 37° C. for 30 minutes. The frequency-dependent storage modulus (G') and loss modulus (G") of the dECM scaffold are measured at 2% strain within a range of 0.1-100 rad/s.

The amount of the dECM loading is set to be 250 μL, and the running GAP is set to be 500 μm. Before running, the dECM that has escaped from the periphery of the cone plate is removed as much as possible with a thin scraper or the like.

(2) Experimental Results

Figure 3A:
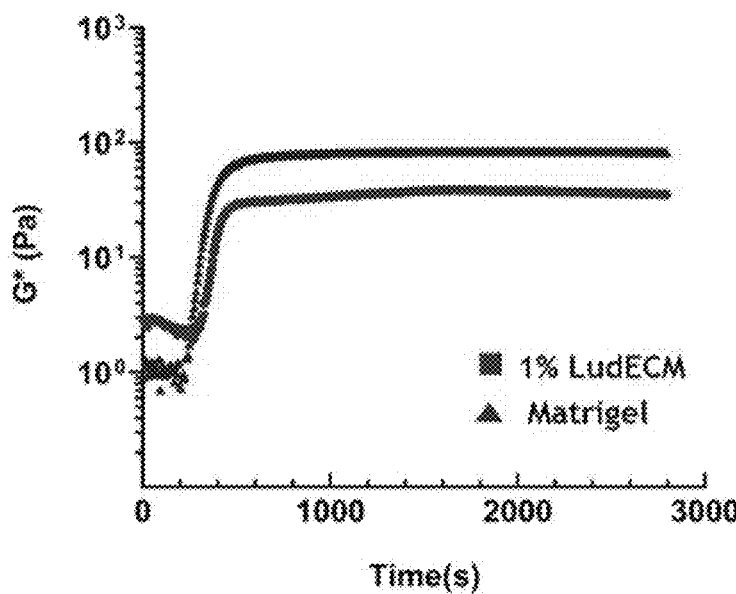
FIGS. 3a and 3b show an analysis of the rheological properties of lung dECM according to an Example of the present invention.
Figure 3B:
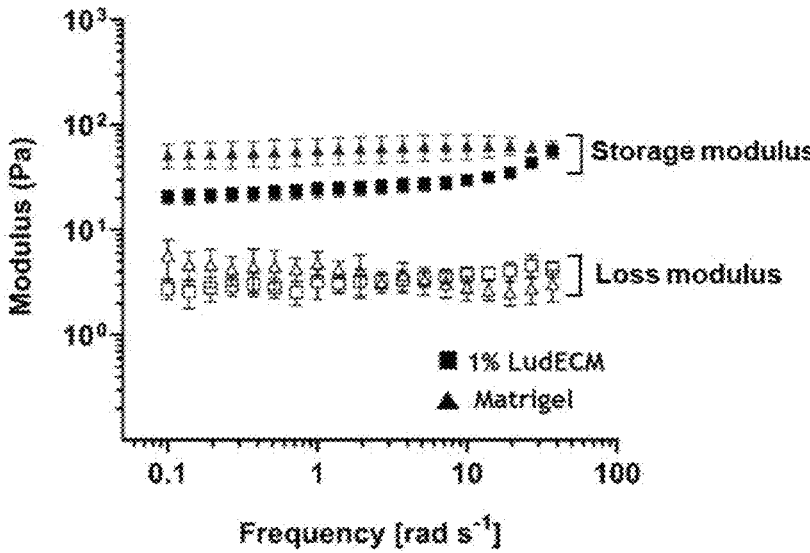
Figure 4A:
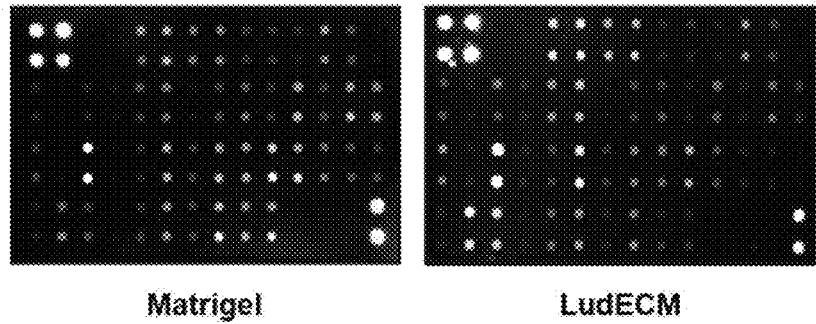
FIGS. 4a to 4e show an analysis of the remaining cytokines in the lung dECM according to an Example of the present invention.
Figure 4B:
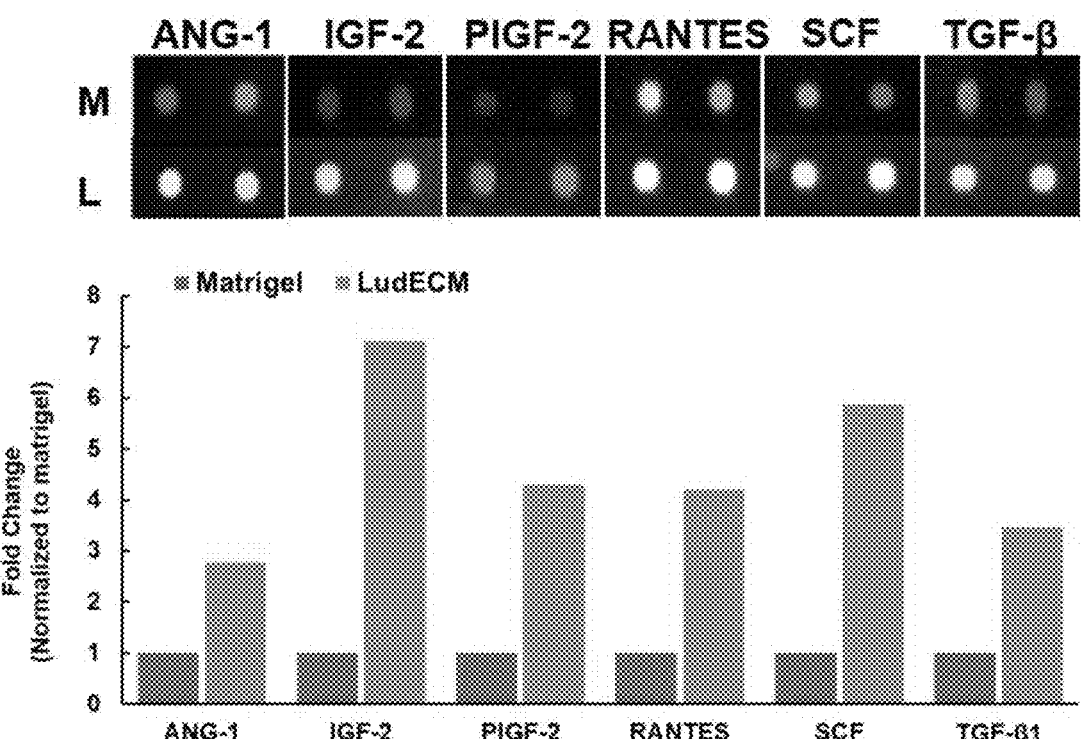
Figure 4C:
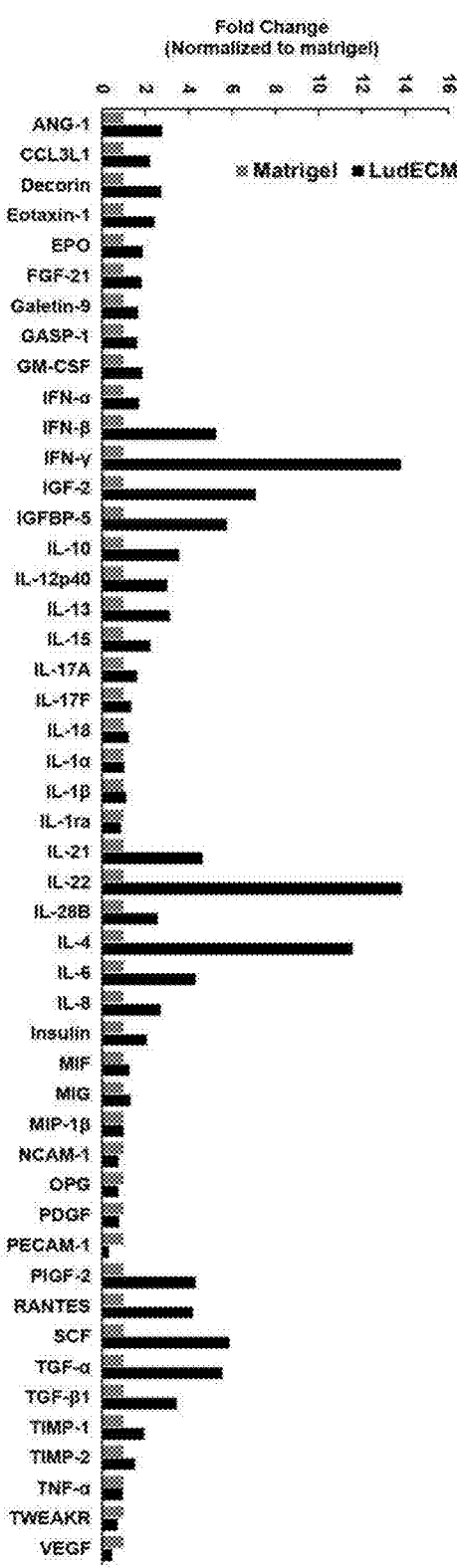
Figure 4D:
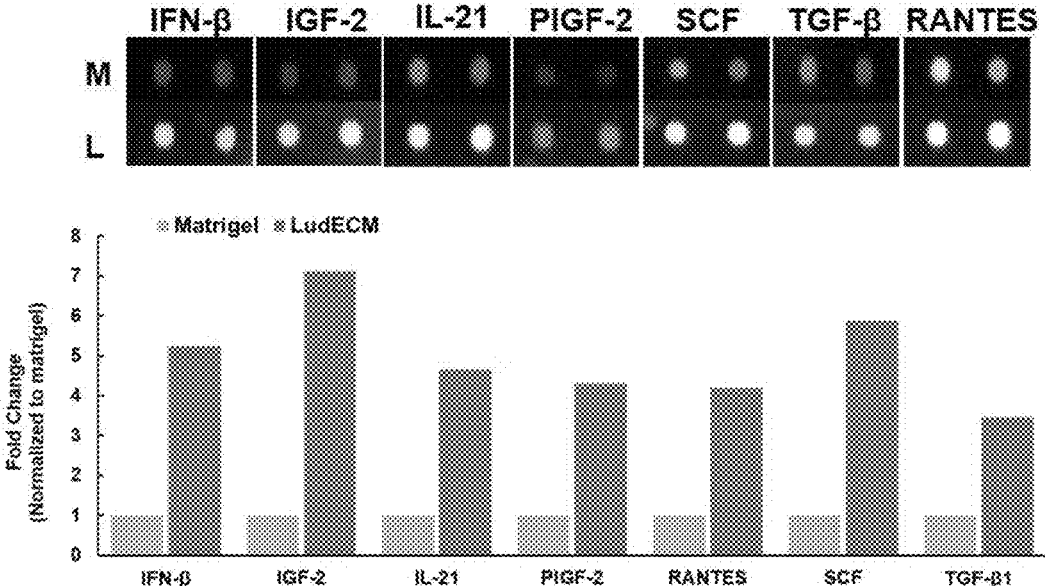
Figure 4E:
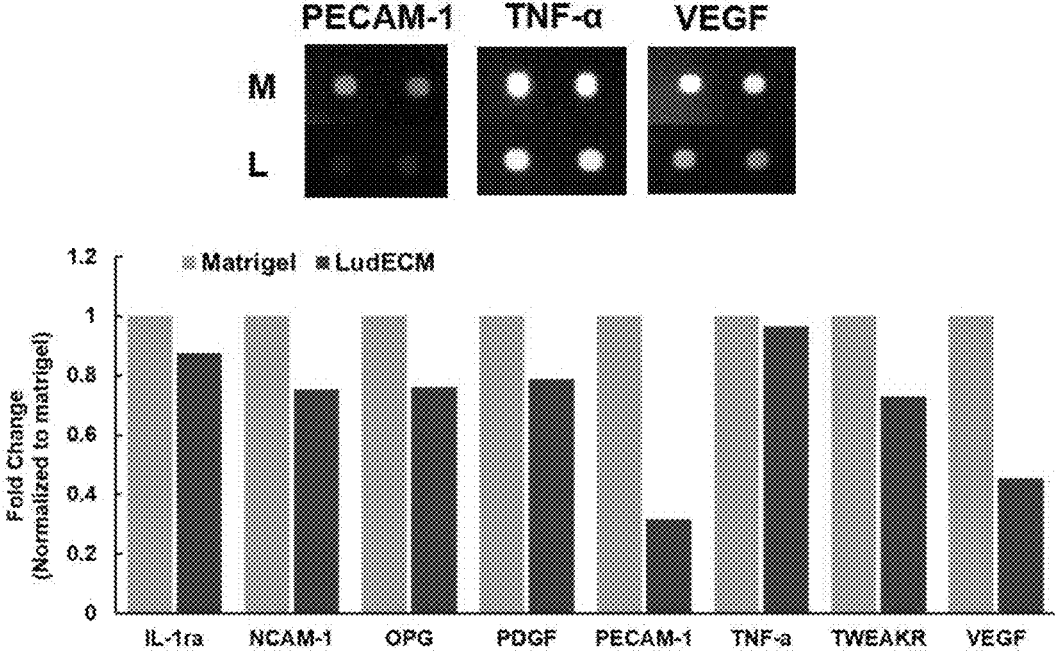

The analytical results are shown in FIGS. 3*a* and 3*b*. MATRIGEL® and the neutralized lung dECM hydrogels exhibit thermal response behavior, show a solution-like phase at a temperature below 15° C., and transform into a gel-like phase (crosslinked gel) when the temperature is increased to a physiological temperature (37° C.). The analysis of the rheological properties of MATRIGEL® and the lung dECM, performed by using a rheometer, showed that stable hydrogels were formed in all groups. MATRIGEL® and the lung dECM showed a drastic increase in the complex modulus in a similar pattern at 37° C. Finally, the neutralized lung dECM showed a fluid-to-gel transition for 50 minutes (FIG. 3*a*). In addition, it was confirmed that the cross-linked lung dECM hydrogel, after the gelation at a physiological temperature (37° C.), exhibited a very stable cross-linking process under dynamic external forces in a range from a low shear frequency to a high shear frequency (0.1-100 rad/s) (FIG. 3*b*).

Example 5: Surface Characterization of Lung dECM Using FE-SEM

The lung dECM scaffold is adjusted to pH 7.

(1) Chemical Dehydration Pretreatment (Application of Lung dECM)

The lung dECM gelated at 37° C. for 30 minutes is immersed in 4% paraformaldehyde to fix. Samples are washed 3 times with 1×PBS for 10 minutes each and 2 more times with running D.W. Ethanol at 30%, 50%, 70%, 90% and 100% is prepared and treated according to the sequence for 10 minutes each.

Hexamethyldisilazane (HMDS) treatment: Since HDMS is a reagent that is harmful to the human body, this process must be carried out in a fume hood. The specific process is described below. ① Treatment is performed at HMDS: 100% ethanol=1:2 for 20 minutes. ② Treatment is performed at HMDS: 100% ethanol=2:1 ratio for 20 minutes. ③ Treatment is performed at 100% HMDS for 20 minutes. ④ After replacing with fresh 100% HMDS, the samples are left in a fume hood overnight to vaporize all of the HDMS solution. After coating with platinum (Pt), imaging is performed.

(3) Experimental Results

Figure 6:
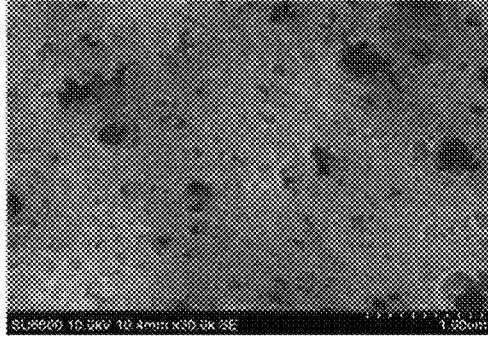
FIG. 6 shows an analysis of the surface structure of the lung dECM using FE-SEM according to an Example of the present invention.
Figure 6:
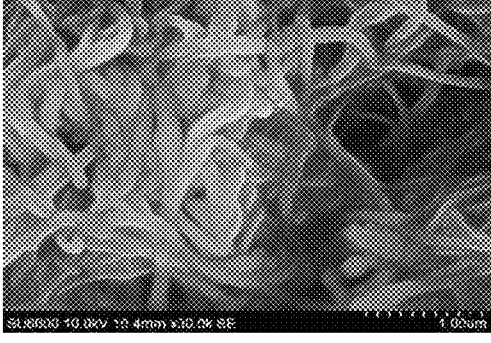

The results are shown in FIG. 6, and it was confirmed that the ECM components were well formed in the form of fiber.

Example 6: Analysis of Residual Cytokines in Lung dECM

(1) Solution Preparation and Lung dECM Scaffold Preparation

(2) Lung dECM Protein Quantification

The lung dECM scaffold is prepared by adjusting the pH to 7. After adding the RIPA buffer to the neutralized dECM, which is kept in ice and subject to a reaction for about 30 minutes. The mixture is mixed well by using a vortex mixer once every 5 minutes. The total protein in the dECM is quantified by using the BCA protein assay kit. The standard is prepared by diluting a 2 mg/mL stock of bovine serum albumin (BSA) with ddH$_2$O. The lung dECM dissociated in the RIPA buffer is used as a stock solution, and samples are prepared by diluting by factors of 2/5/10/50/100/200/500/ 1000 times with ddH$_2$O. The standard and the samples are loaded in triplicate into a 96-well plate at 20 μL/well each. The blank is the RIPA buffer. The required amount of the BCA solution is calculated, and Solution A and Solution B are mixed at the ratio of 49:1. It should be ensured that the tube is wrapped with aluminum foil, and Solution A and Solution B solutions are not mixed in advance but are mixed after loading the samples. The mixed solution is poured into the reservoir and loaded at 160 μL/well each by using a multi-channel pipettor. The entire 96-well plate is wrapped with aluminum foil and subject to a reaction in an incubator at 37° C. for 30 minutes. The absorbance is measured at a 540 nm wavelength with a microplate reader. A standard curve is drawn and the total protein in the samples is calculated. The dilution factor was determined within the recommended protein loading range (load 50 to 500 μg of total protein) provided in the cytokine array protocol. The diluted solution was prepared by diluting the lung dECM stock solution to a concentration of 50 μg/mL so that the total protein became 50 μg. The analysis method was carried out in the same manner as the manufacturer's protocol (RayBio® C-Series Porcine cytokine array 1).

(3) Experimental Results

The results are shown in FIGS. 4*a* to 4*e*, and FIGS. 4*a* to 4*e* show the results of analyzing the residual cytokines in the lung dECM. Among them, it was confirmed that stem cell growth factor (SCF) was present in the lung dECM more than twice as high as MATRIGEL®. In particular, it was confirmed that angiopoietin 1 (AGN-1), which plays a very important role in the blood vessel development and angiogenesis and which also plays a pivotal role in mediating the interaction of endotheliocytes and their surrounding matrix with mesenchymal cells, is present in the lung dECM in a large amount. In addition, major factors affecting organoid culture, such as insulin-like growth factor (IGF), TGF-β, or placental growth factor (PIGF), are contained in a large amount, compared to MATRIGEL®. Therefore, the lung dECM contains a large amount of cytokines produced and secreted by immune cells, vascular cells, and other stromal cells in actual tissues, and thus can mimic the tissue microenvironment more similarly. In particular, in addition to the provision of extracellular matrix, the lung dECM contains cytokines related to angiogenesis and cell proliferation in a large amount, and thus is more effective in the organoid culture than MATRIGEL®

Example 7: Evaluation of Histological Characteristics of Lung dECM

Tissue staining (Hematoxylin & Eosin, Masson's trichrome stain) of the lung dECM prepared in Example 1 was performed.

Figure 5:
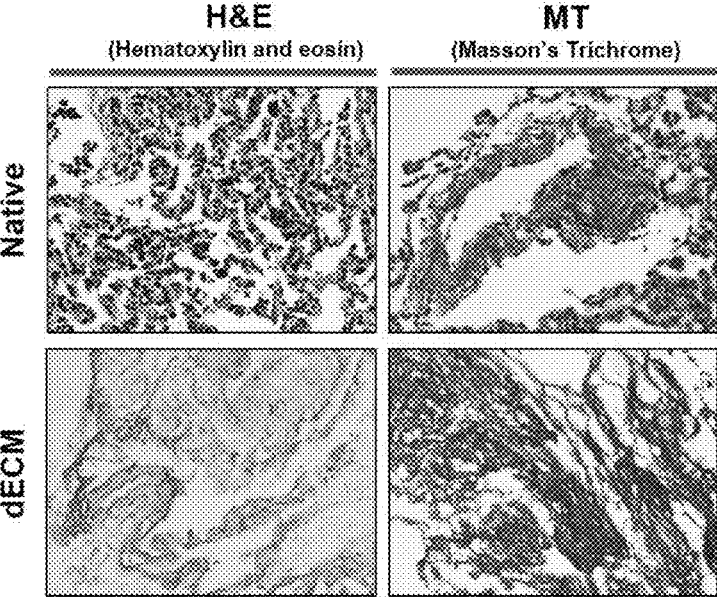
FIG. 5 shows an analysis of the histological characteristics of the lung dECM according to an Example of the present invention.

As shown in FIG. 5, the histological (H & E, MT staining) analysis confirmed that the cells were removed from the tissue after the decellularization process, while the extracellular matrix component mimicking the biochemical microenvironment was maintained.

Example 8: Analysis of Residual Protein in Lung dECM

The residual protein of the lung dECM prepared in Example 1 was analyzed by using LC-MS/MS (Liquid Chromatography-Mass spectrometry).

(1) Sample Pretreatment

Protein unfolding: In order to split the remaining protein into peptide fragments, it is first lysed in a buffer to break the covalent bond.

Deglycosylation: This is a process that is specifically applied to glycoproteins. Since glycoproteins have sugar chains in the middle of the sequence and the sugar chains may cause problems in the mass value later, the sugar portions are removed and the glycoprotein portions are changed into the forms of normal peptides.

Digestion: Proteins are decomposed with LysC/Trypsin, etc.

Clean up Detergents such as SDS and salt components in the buffer are removed. This process must be taken for accurate detection of peptide ions because salt interference can be problematic.

(2) Analysis Using LC-MS/MS

The database of the individuals is imported and analyzed by using the sequence library.

(3) Experimental Results

Figure 7:
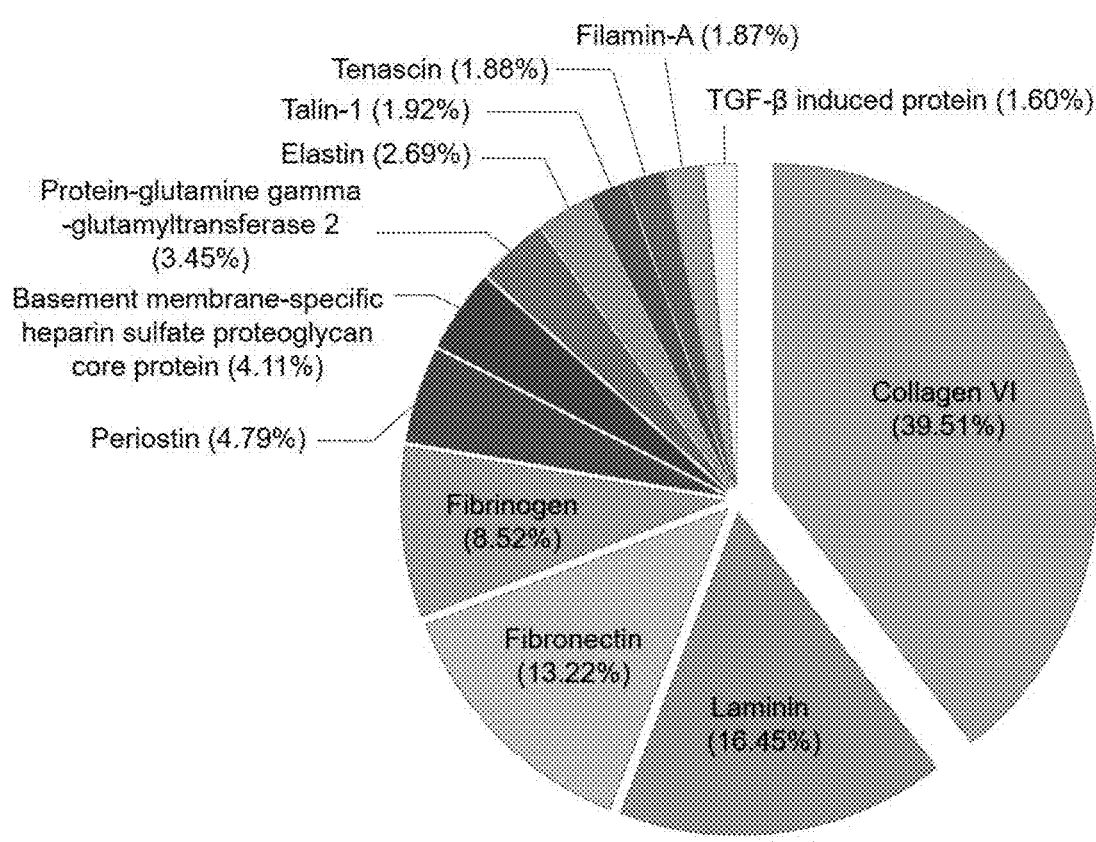
FIG. 7 shows an analysis of the protein components of the lung dECM using LC-MS/MS according to an Example of the present invention.

As shown FIG. 7, the experimental results confirmed that the lung dECM contained a large amount of collagen VI, which is related to cell survival and functional improvement. It was also confirmed that laminin, which is an important factor to the organoid culture, was present in a large amount and in addition to laminin, fibronectin, which is important for cell adhesion, growth and differentiation, was present in a large amount. Additionally, the results confirmed that tissue-specific extracellular matrix proteins remained even after the decellularization process so that the decellularization-based lung dECM scaffold developed in the present invention can help the organoid growth and improve the organoid differentiation and functions.

Example 9: Selection of Formulations Compatible for Organoid Culture

To perform organoid culture with the lung dECM, which had been completely prepared for the use as a support, hydrogel formulation conditions similar to the gelation tendency of a scaffold (MATRIGEL®) that is often used for organoid culture were screened. The verification was performed by using the dECM alone or by using a mixture of MATRIGEL® and the dECM.

(1) Selection of Formulations Compatible with Lung dECM Organoid Culture

The lung dECM was tested based on the concentrations of 2%, 1.5%, and 1%, and subsequent experiments were conducted only based on the concentrations of 2% and 1%. The dECM at each concentration was used alone or mixed with MATRIGEL® (dECM:MATRIGEL® ratio=8:1, 4:1, 2:1, 1:1, 1:2) for comparison. The overall details are similar to "Example 4: Rheological Characterization of Lung dECM".

(2) Gelation Tendency (Sol-Gel Transition) and Frequency Sweep Analysis of Scaffold To evaluate the rheological properties, the lung dECM scaffold is prepared by adjusting the pH thereof to 7-7.5. The measuring plate PP25 is mounted on the rheometer to perform the evaluation. The amount of dECM loading is 300 μL or more, and the running GAP is set to 300 μm for the lung. Before running, the dECM that has escaped from the periphery of the measuring plate is removed as much as possible with a scraper. The sol-gel transition, complex viscosity, and frequency sweep of the dECM scaffold are measured by creating an experiment under the following conditions in the installed software program (RheoCompass 1.19).

Gelation kinetics: The dECM support is placed on a plate, and the storage & loss modulus of the dECM support is measured under the conditions of 2% strain, 100 rad/s, and 2° C./min at 4-37° C. for 30 minutes to calculate the sol-gel transition tendency and complex viscosity ($\eta^*$).

Frequency sweep: The frequency-dependent storage modulus (G') and loss modulus (G") of the completely gelated dECM scaffold is measured by changing the frequency from 500 rad/s to 1 rad/s at 2% strain and at 37° C.

(3) Experimental Results

Figure 8A:
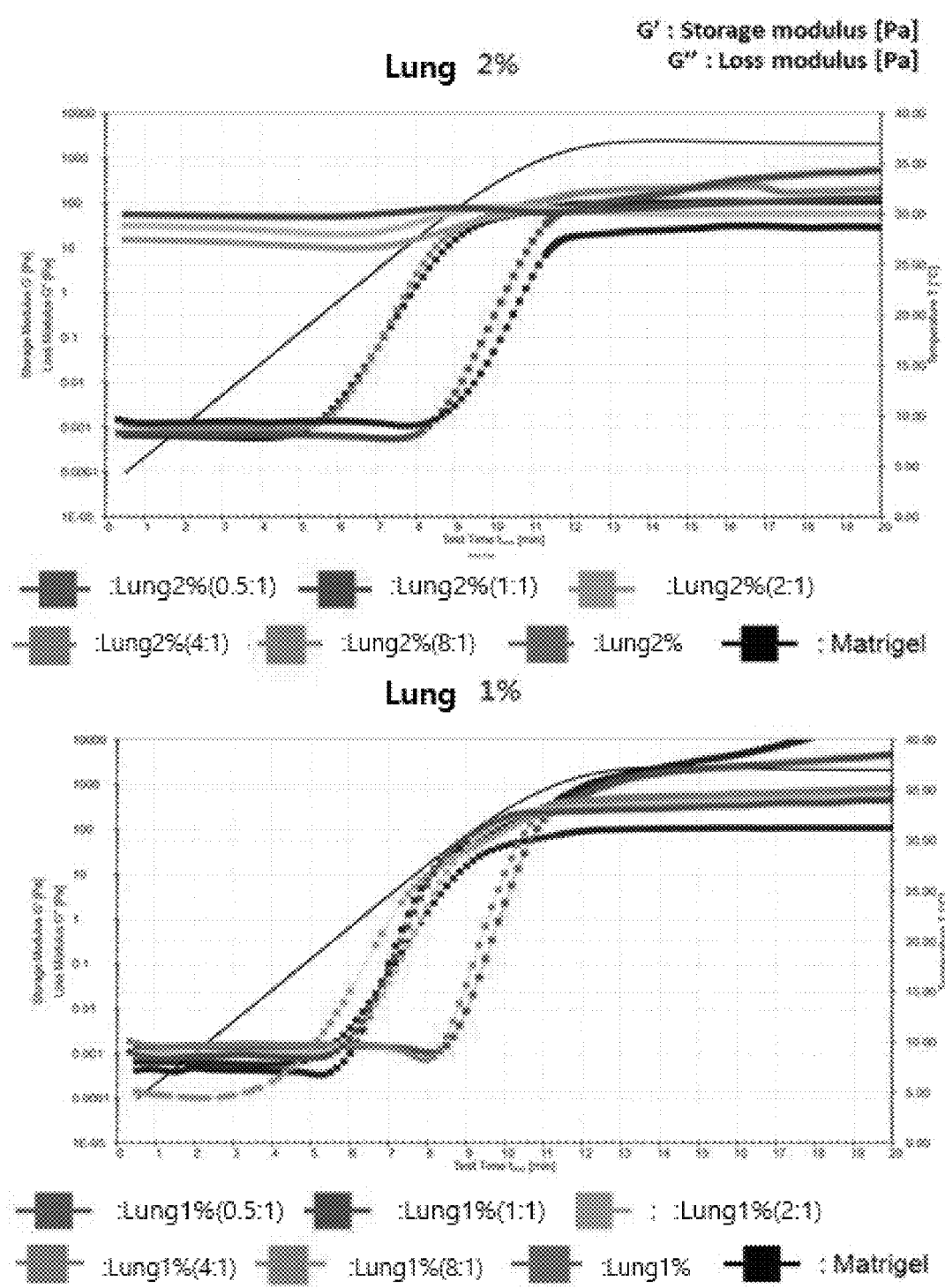
FIGS. 8a and 8b show an analysis of the gelation tendency (sol-gel transition) for selecting compatible culture conditions of lung organoids according to an Example of the present invention.
Figure 8B:
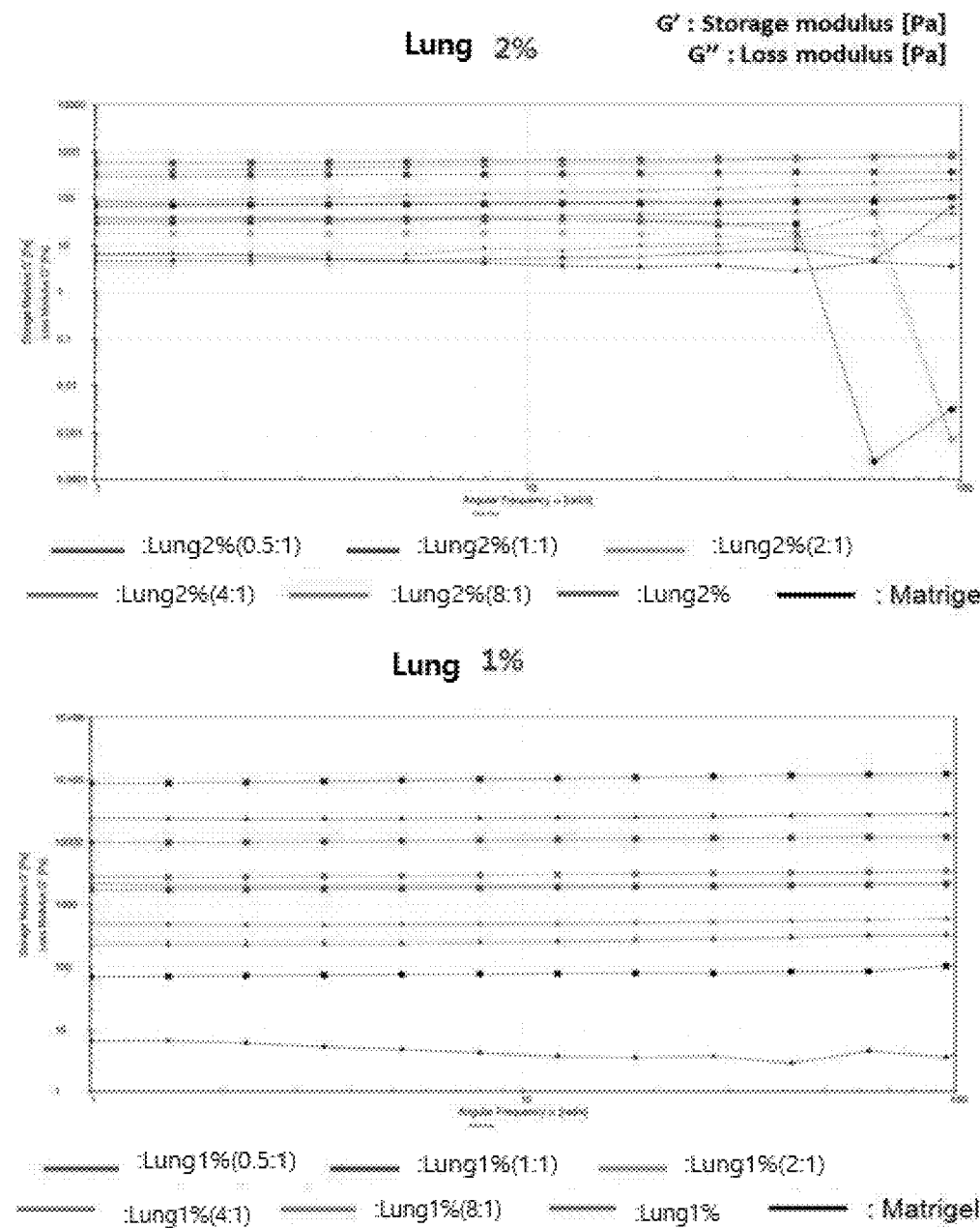

The results are shown in FIG. 8*a* (gelation kinetics) and FIG. 8*b* (frequency sweep). As in Example 8, MATRIGEL® and neutralized lung dECM hydrogels exhibit thermal reaction behavior and a solution-like phase at a temperature of lower than 5° C. As the temperature increases to 37° C., the same as in the body, it is transformed into a gel-like state. The sol-gel transition and frequency sweep were analyzed by a rheometer with MATRIGEL® as a control, with the lung dECM alone, and with the mixed gels prepared by mixing the same with MATRIGEL® at the ratios described in Example 9 (1), and the results observed from each organ are described below.

FIGS. 8a and 8b show the results of analyzing the dECM alone and the mixtures prepared by mixing the same with MATRIGEL® at the ratios described above, after preparing the lung dECM at 2% and 1% according to one embodiment. In the experiment based on the lung 2% dECM, gelation was observed in the control (MATRIGEL®) and the mixtures prepared mixing at the dECM-to-MATRIGEL® ratios of 0.5:1, 1:1 and 2:1 among the ratios described in Example 9 (1). In the experiment based on the lung 1% dECM, gelation was all observed in the control (MATRIGEL®) and the experimental groups described above. However, stable gelation was observed only in the lung 1% dECM and the mixture prepared at the dECM-to-MATRIGEL® ratio of 8:1 among the ratios described in Example 9 (1). According to analytical results of the viscoelasticity (frequency sweep) of the hydrogel of the lung dECM gelated at 37° C. and mixtures thereof, even in the experimental group in which gelation was performed stably as described above, the physical properties stably expected from the culture, similarly to MATRIGEL®, were observed in the 1% dECM alone and the mixture prepared at the dECM-to-MATRIGEL® ratio of 8:1. The formulation compatible with the organoid culture based on the neutralized lung dECM is based on the lung 1% dECM alone and the mixture prepared at the ratio dECM-to-MATRIGEL® ratio of 8:1.

Finally, the neutralized lung dECM and the mixture prepared at the selected ratio based on the results described above among the mixtures described in Example 8 were subject to gelation for 30 minutes (FIG. 8a), and it was confirmed that after the hydrogel was stabilized, they had physical properties that are similar to those of MATRIGEL® under a dynamic external force in the range from a high shear frequency to a low shear frequency (500-1 rad/s) (FIG. 8b). In Example 8, in consideration of gelation stabilization, gelation was performed at 37° C. for 40 minutes or longer.

Example 10: dECM-Based Organoid Culture

To evaluate the organoid culture compatibility of the lung dECM that has completely been prepared for use as a scaffold, organoid culture is performed based on the dECM.

(1) Human-Derived Lung (Tumor or Normal) Organoid Culture and dECM Embedding

To culture a human-derived lung organoid, based on Advanced DMEM/F12, a medium is prepared by mixing Glutamax, HEPES, and Anti-anti. For the lung organoid culture, growth factors such as Rspondin-1, B27, nicotinamide, N-acetylcysteine, SB202190, A83-01, mNoggin, hFGF10, mFGF7, and Primocin are added. To culture in the dECM the lung organoid that is being cultured, the organoid that is being cultured in MATRIGEL® is recovered.

The specific process is described below. ① The MATRIGEL® in which the lung organoid is growing is physically destroyed through pipetting. ② The organoid is disassembled with a syringe and a needle. ③ Pipetting is additionally performed by using a 10 ml tip. ④ Centrifugation is performed at 4° C. and 200×g for 5 minutes. ⑤ The supernatant is removed to obtain an organoid pellet. ⑥ The organoid pellet of 5 is washed by pipetting with a medium prepared based on Advanced DMEM/F12 by mixing Glutamax, HEPES, and Anti-anti. ⑦ Centrifugation is performed at 4° C. and 200×g for 5 minutes. ⑧ The supernatant is removed to obtain an organoid pellet. ⑨ The amount required for embedding is calculated and the organoid pellet is mixed with the dECM scaffold made in Example 3 (a mixture prepared according to the mixing ratio of MATRIGEL® and dECM). ⑩ The dECM mixture of 40-50 μl is dropped into a 24-well plate (or culture plate). ⑪ Incubation is performed at 37° C. for 30-40 minutes. ⑫ The organoid culture medium containing Y-27632 is added. ⑬ The medium is replaced by an organoid culture medium that does not contain Y-27632 once every 2-3 days. ⑭ After 7-14 days following the subculture, depending on the state of the organoid, subculture is performed for long-term culture (more than 30 days).

Example 11: Cytotoxicity Evaluation of dECM-Based Organoids

To evaluate the culture compatibility of the organoid cultured on the dECM scaffold, live cells are confirmed by a Live/Dead assay to confirm that the dECM scaffold is non-toxic to the organoid culture.

(1) Live/Dead Assay of Organoid in dECM-Based Culture

The toxicity of the dECM scaffold was confirmed by staining and observing the live cells and dead cells of the organoid cultured in the dECM by using the Invitrogen Live/Dead® Viability/Cytotoxicity Kit. The dECM scaffold in which organoid is being cultured is washed with pre-warmed DPBS (1×) 3 times for at 37° C. for 5 minutes each. Afterwards, the method was performed in the same manner as the manufacturer's protocol.

(2) Experimental Results

Figure 9A:
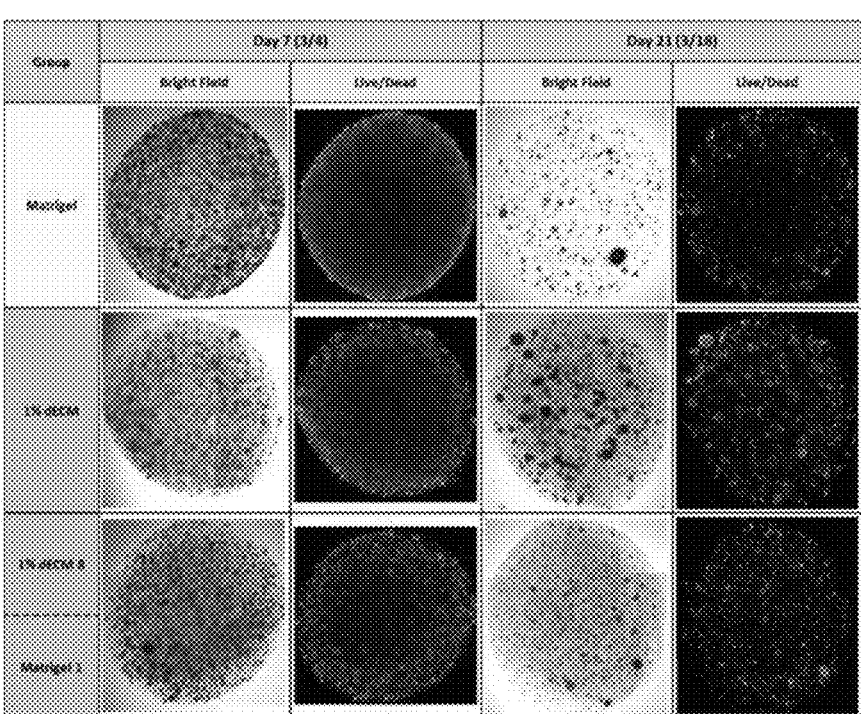
Figure 9B:
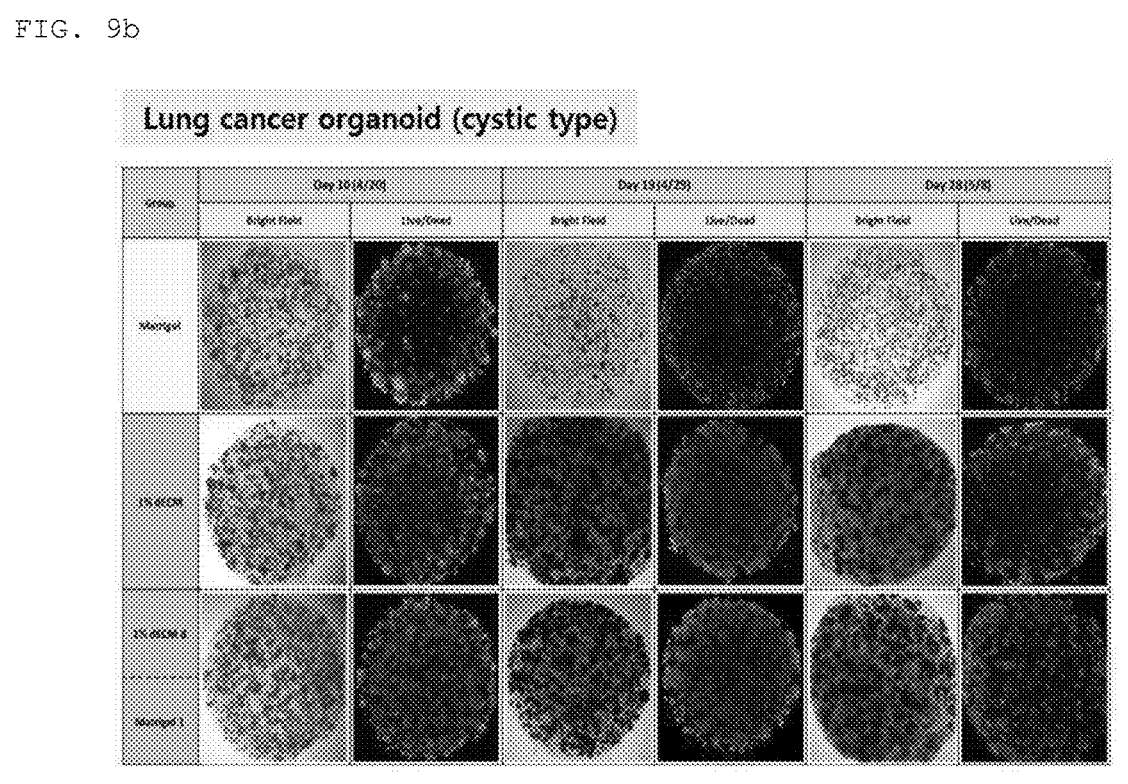

As shown in FIGS. 9a and 9b, the experimental results confirmed that there is no cytotoxicity in culturing organoids in the lung dECM prepared according to an Example of the present invention and in the organoid culture-compatible hydrogel selected in Example 9.

As shown in FIGS. 9a and 9b, when the human-derived lung tumor organoid is cultured in the 1% lung dECM and in the hydrogel prepared by mixing the 1% lung dECM with MATRIGEL® at a ratio of 8:1, the culture was similar to or better than the culture in MATRIGEL® without toxicity.

Example 12: Evaluation of Proliferation of dECM-Based Organoids

To evaluate the culture compatibility of the organoid cultured on the dECM scaffold, the proliferation potential of the organoid in the dECM is evaluated with the CCK-8 assay, which confirms whether the organoid cultured on the dECM scaffold proliferates based on the respiration rate of the cells.

(1) dECM-Based CCK-8 Assay of Organoid in Culture

The proliferation of an organoid (and cell) being cultured in the dECM was confirmed by measuring the respiration volume of the organoid cultured in the dECM by using DOJINDO's CCK-8 assay kit. The dECM scaffold in which the organoid is being cultured is washed with pre-warmed DPBS (1×) 3 times at 37° C. for 5 minutes each. Afterwards, the method was performed in the same manner as the manufacturer's protocol. In the analysis of the results, the occurrence of the proliferation was confirmed by comparing the absorbance values of the samples for each period.

(2) Experimental Results

Figure 10:
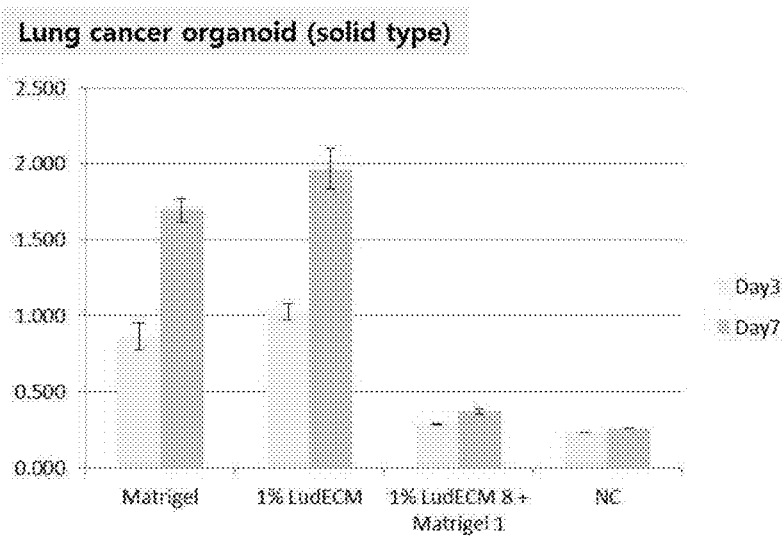
FIG. 10 shows the results of the evaluation of the proliferation of the lung tumor organoids within the limits performed by using the CCK-8 analysis method according to an Example of the present invention. According to the order, the analytical results are the proliferation tendencies obtained by culturing the solid type and the cystic type among the human-derived lung tumor organoids based on the lung 1% dECM under the conditions of using the dECM alone and mixing with MATRIGEL® according to the presented ratios. G1: MATRIGEL®, G2: 1% lung dECM, and G3: 1% lung dCEM 8+MATRIGEL® 1.
Figure 10:
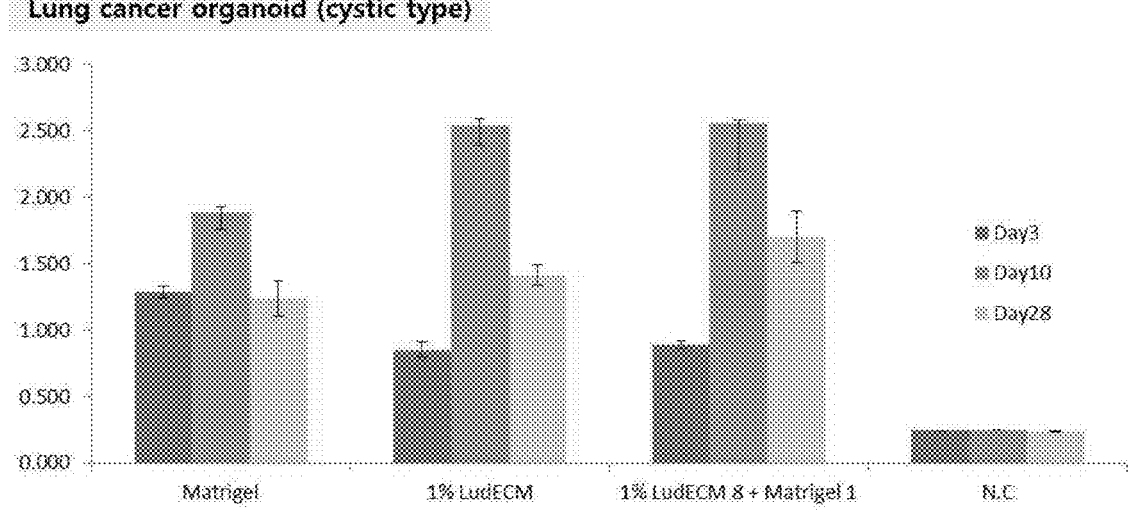

The results are shown in FIG. 10, confirming the cell proliferation tendency when culturing the organoid based on the lung dECM. N. C, referring to a negative control value, was measured in a blank in the absence of cells.

The results showed that in the case of culturing a patient-derived lung tumor organoid based on the lung dECM, in the solid type tumor organoid, the organoid culture proliferation effect when the 1% lung dECM was used alone was similar to or better than that of MATRIGEL® (FIG. 10b).

Finally, it was confirmed that there was a similar or superior effect on the organoid proliferation in the 1% lung dECM than in MATRIGEL®.

Example 13: Validation of Culture Effectiveness of dECM-Based Human-Derived Lung Tumor Organoid To evaluate the culture compatibility of the tumor organoid cultured on the dECM scaffold, it is confirmed whether the tumor organoid cultured on the dECM scaffold is effective with the tumor organoid cultured on the scaffold which is often used in the organoid culture (MATRIGEL®).

(1) Extraction of Genomic DNA from Human-Derived Lung Tumor Organoid Cultured in the Lung dECM and MATRIGEL®

The scaffold and MATRIGEL® on which the human-derived lung tumor organoid is growing is obtained by physical destroying the same through pipetting. Centrifugation is performed by table-top or a centrifugation by using microcentrifuge at 13,000 rpm. The supernatant is removed, leaving only the human-derived lung tumor organoid pellet. The genomic DNA was extracted by using HiGene™ Genomic DNA prep Kit. The following procedures were carried out in the same manner as described in the animal tissue manual of the manufacturer's protocol.

(2) Performing Sequencing to Confirm Mutation Type of Human-Derived Lung Tumor Organoid In order to confirmed whether the mutation type of each organoid is the same as that of the control, sequencing of the genomic DNA extracted in (1) is performed. The sequencing was performed by direct sequencing, and was commissioned by Macrogen.

(3) Experimental Results

Figure 11:
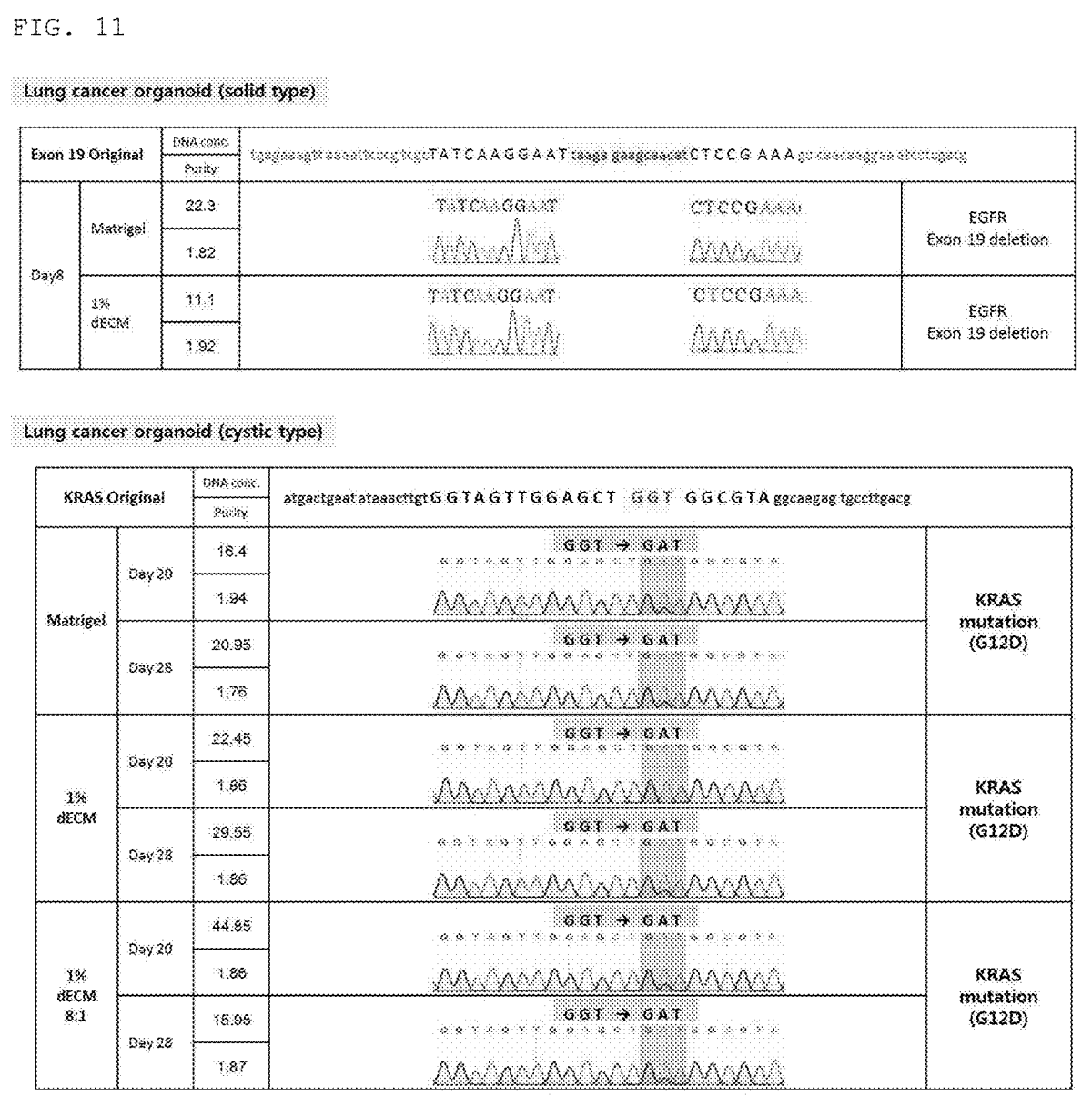

FIG. 11 shows the experimental results of confirming by the direct sequencing whether, among the markers for distinguishing tumors, the mutations and positions thereof are retained the same as those of human-derived tumors, in order to verify the effectiveness of the human-derived tumor organoid cultured in the lung dECM-based hydrogels. As shown in FIG. 11, a tumor organoid having the Exon 19 deletion mutation, which is a typical mutation of lung cancer, and tumor organoids having the KRAS mutation were cultured in the lung 1% dECM, wherein the tumor organoid having the Exon 19 deletion mutation was cultured for 8 days and the tumor organoids having the KRAS mutation were each cultured for 20 days and 28 days, and the results showed that each of the mutations and the position thereof were retained.

Figure 12A:
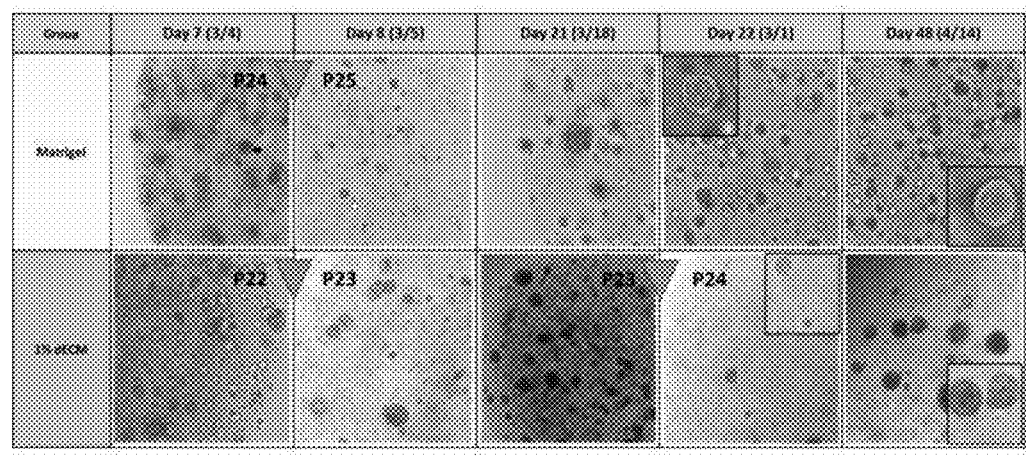
FIG. 12a shows the results of microscopic observation of the long-term culture of the solid type and FIG. 12b shows those of the cystic type for 48 days and 28 days, respectively.
Figure 12B:
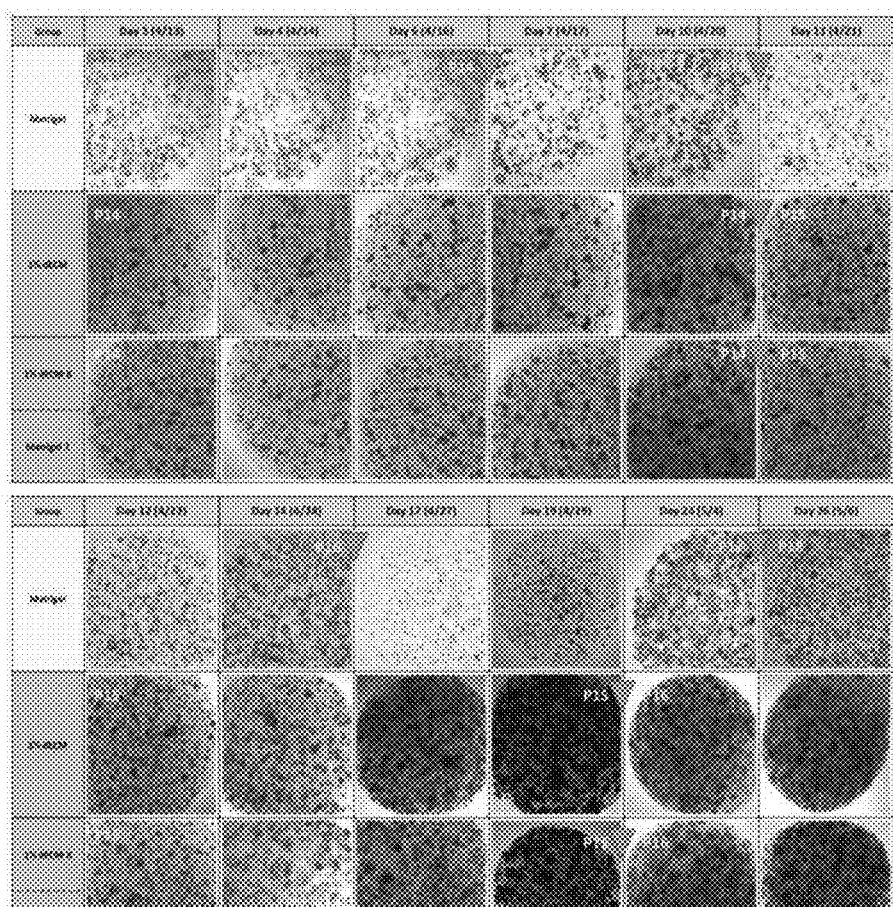
Figure 12B:
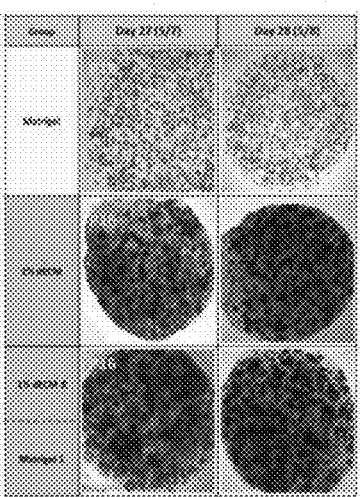

In addition, long-term culture of the human-derived lung tumor organoid was performed according to an Example of the present invention in order to confirm the possibility of long-term culture of the lung tumor organoid cultured in the dECM. Therefore, FIG. 12a shows the results of the microscopic observation of the long-term culture of the solid type for 48 days among the human-derived lung tumor organoids based on the 1% lung dECM prepared according to an Example of the present invention under the conditions of using the dECM alone and mixing the same with MATRI-GEL® according to the ratios described above, wherein FIG. 12b shows the results of the long-term culture of the cystic type for 28 days and FIG. 12a shows the analytical results of the cytotoxicity of the organoid on Day 17, Day 30 and Day 44 during the culture of the solid type for 48 days. The results confirmed that the scaffold of the present invention maintains excellent properties in the long-term culture of the tumor organoids.

Example 14: Verification of Effects by Stirring Time and Stirring Speed of the S4) Lysing This Example describes the experimental method in which the stirring time and speed were varied in the S4) lysing according to the present invention, and the results obtained therefrom.

(1) Experimental Method

The experimental method was carried out based on the methods described in Example 2 and Examples 10 to 12 of the present invention.

In order to prepare dECMs with different stirring time and speed, a decellularization composition was prepared according to the method of Example 2 of the present invention.

First, in order to prepare dECM with different stirring time, the pulverized dECM prepared in Example 2 was put into a 50 mL conical tube, and 0.5 M acetic acid was added together with pepsin and lysed at a stirring speed of 330 rpm for 24 hours, 72 hours, 96 hours and 120 hours, respectively.

In addition, in order to prepare dECM with different stirring speed, the mixture was lysed at a stirring speed of 80 rpm, 150 rpm, 330 rpm, 500 rpm, 800 rpm, and 1000 rpm for 96 hours. The lysed dECM was filtered by using a cell strainer to filter out the lung dECM powder that was not lysed.

Subsequently, in order to adjust the pH of the prepared decellularization composition, 10×PBS and 10 N sodium hydroxide (NaOH) were added, wherein the PBS and NaOH were stored at a refrigerated temperature before use and used in a cold state for the pH adjustment.

In addition, in order to test the organoid culture depending on the stirring speed and the stirring time, first, the lung organoid was cultured according to the method of Example 10 of the present invention.

In order to encapsulate the cultured lung organoid in the dECM, the lung organoid was obtained with a 1000 μl tip and a pipette according to the method of Example 10 of the present invention, and collected in a conical tube. After that, the organoid was primarily disassembled by using a syringe and a needle, and then pipetting was additionally performed with a 10 ml tip and a pipette aid. The disassembled organoid was obtained by subjecting the same to centrifugation and removing the supernatant.

The number of the organoids required for this experiment and the required amount of the dECM were calculated by calculating an appropriate sub-culture ratio depending on the state of the organoid (40 µl dECM required per dome). The calculated amount of the organoid pellet was mixed with each of the dECMs prepared by applying different stirring time (24 hours, 72 hours, 96 hours, 120 hours) and stirring speed (80 rpm, 150 rpm, 330 rpm, 500 rpm, 800 rpm, 1000 rpm), and the resulting mixtures were encapsulated. The dECM mixed with organoids was dropped in an amount of 40 µl onto a culture plate by using a pipette to form a dome for organoid culture, which was the subject to gelation at 37° C. for 30-40 minutes. After that, an organoid culture medium was added, and the added medium was replaced with new one once every 2-3 days. Four days after the encapsulation of the organoid, the culture state of the organoid was observed by the method of Examples 11 and 12 according to the present invention.

(2) Experimental Results

The physical properties of the lung dECM and the results of the organoid culture for each stirring time are shown in FIGS. 13 to 16.

Figure 13:
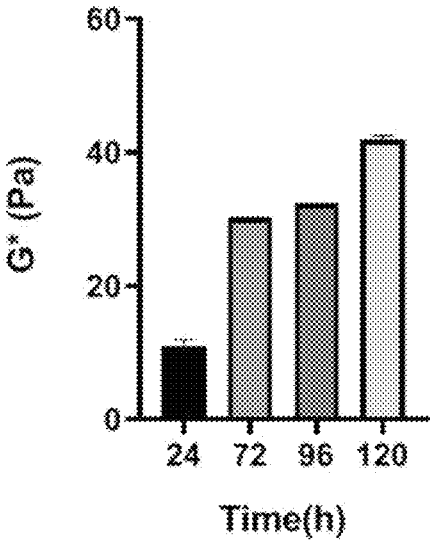
FIG. 13 is a graph showing the modulus values of the lung dECM when the stirring time was changed in the S4) lysing according to an Example of the present invention.
Figure 14:
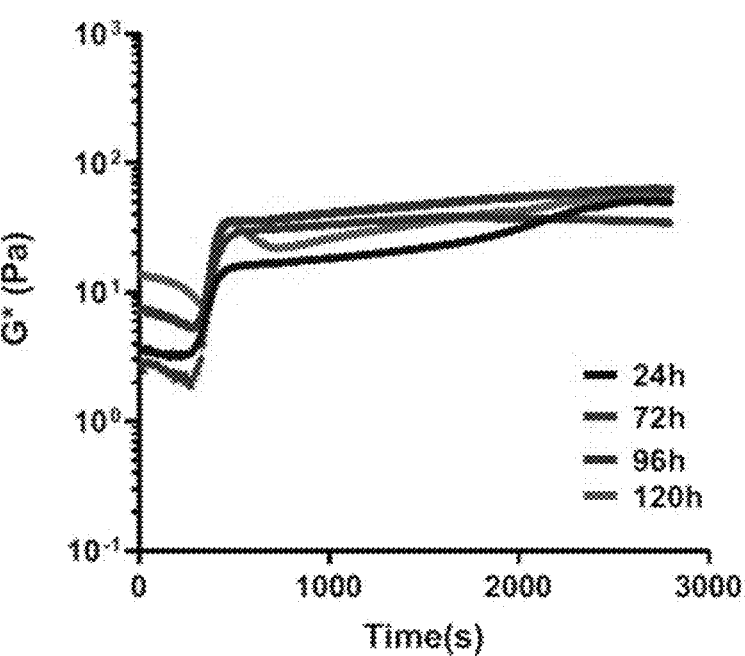
FIG. 14 is a graph showing the gelation kinetic value of the lung dECM for each stirring time in the S4) lysing according to an Example of the present invention.
Figure 15:
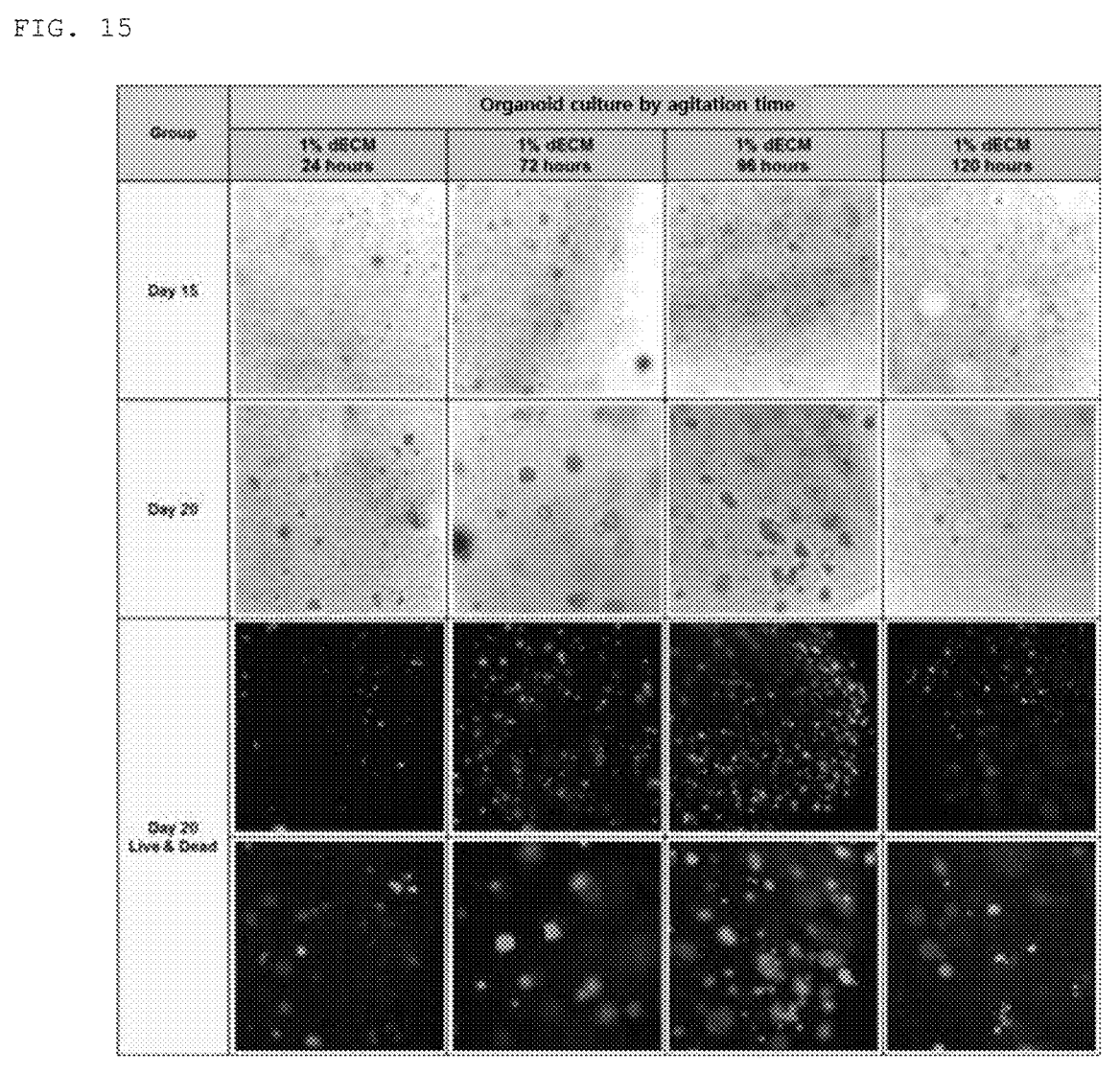
Figure 16:
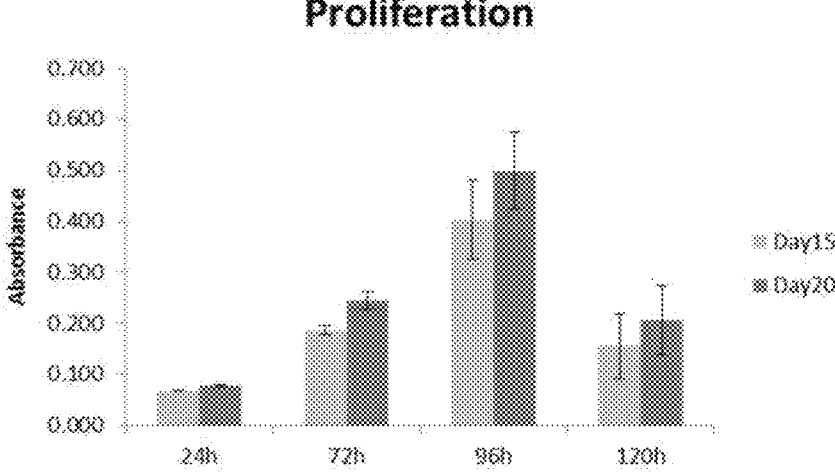
FIG. 16 is a graph showing the proliferation rate of the lung organoid culture for each stirring time in the S4) lysing according to an Example of the present invention.

FIG. 13 is a graph showing the modulus value of the lung dECM when the stirring time was changed in the S4) lysing according to an Example of the present invention; FIG. 14 is a graph showing the gelation characteristic (gelation kinetic) value of the lung dECM for each stirring time; FIG. 15 is a photograph showing the lung organoid culture state for each stirring time; and FIG. 16 is a graph showing the proliferation rate of the lung organoid culture for each stirring time.

As shown here, the modulus value, representing the physical properties for each stirring time, was in the order of 24 h<72 h≒96 h<120 h. Therefore, it was confirmed the physical properties were best when the stirring time was 72-96 hours (FIGS. 13 and 14).

In addition, although the physical properties continued to increase when the stirring time was 120 hours, a lot of air bubbles were generated when the organoid was encapsulated, which made the experiment difficult. In particular, in the dECM that was stirred for 24 hours and 120 hours, a lot of organoid deaths occurred, indicating that the physical properties of the organoid culture are important. In addition, it was found that the culture tendency was improved in the order of 24 h<72 h≒96 h>120 h (120 h<72 h) in the organoid culture (FIGS. 15 and 16).

Accordingly, the present inventors learned that the conditions compatible with the organoid culture are 72-96 hours in terms of the stirring time.

In addition, the physical properties of the lung dECM and the organoid culture results for each stirring speed are as shown in FIGS. 17 to 20.

Figure 17:
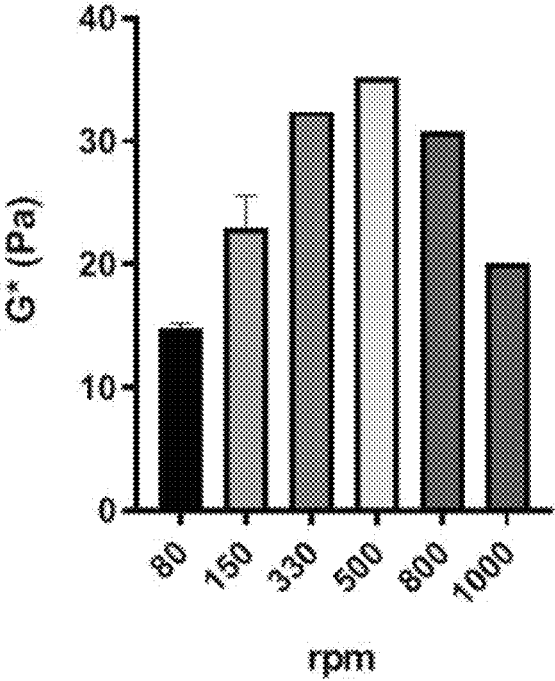
FIG. 17 is a graph showing the modulus value of the lung dECM when the stirring speed was changed in the S4) lysing according to an Example of the present invention.
Figure 18:
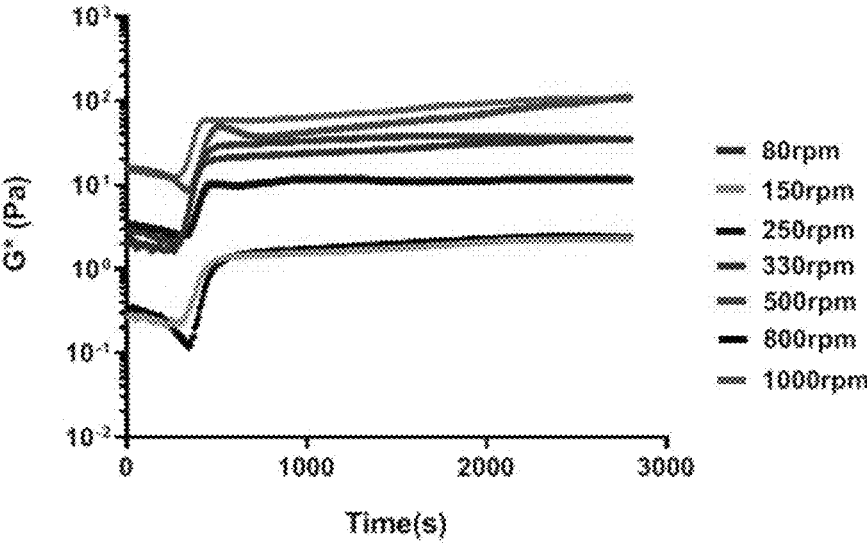
FIG. 18 is a graph showing the gelation kinetic value of the lung dECM at each stirring speed in the S4) lysing according to an Example of the present invention.
Figures 19, 20:
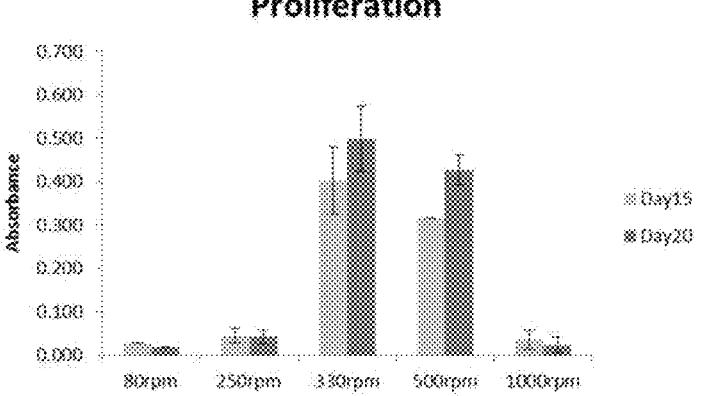
FIG. 19 is a photograph showing the culture state of the lung organoids at each stirring speed in the S4) lysing according to an Example of the present invention.
FIG. 20 is a graph showing the proliferation rate (proliferation) of the lung organoid culture according to the stirring speed in the S4) lysing according to an Example of the present invention.

FIG. 17 is a graph showing the modulus value of the lung dECM when the stirring speed was changed in the S4) lysing according to an Example of the present invention; and FIG. 18 is a graph showing the gelation characteristic (gelation kinetic) value of the lung dECM for each stirring speed, FIG. 19 is a photograph showing the lung organoid culture state for each stirring speed; and FIG. 20 is a graph showing the proliferation rate of the lung organoid culture for each stirring speed.

As shown here, the modulus value, representing the physical properties for each stirring speed, was in the order of 80<150<330≤500>800>1000 (80<1000<150<800<330<500) rpm, and it was confirmed the physical properties were best when the stirring speed was 330-500 (FIGS. 17 and 18).

In addition, In addition, it was confirmed that in the organoid culture, the culture efficiency was in the order of 80 ≒250≪330≒500≫1000 (80≒250≒1000≪330≒500), and dome formation was impossible at 80 rpm. In particular, in the dECM stirred at 80, 250, and 1000 rpm, a lot of organoid deaths occurred and no live organoid was observed, indicating that the physical properties of the organoid culture are important, and appropriate conditions could be set accordingly (FIGS. 19 and 20).

Therefore, the present inventors learned that the conditions compatible with the organoid culture are 330-500 rpm in terms of the stirring speed.

Example 15: Verification of Effect of Each Condition of the S5) Adjusting pH This Example describes the experimental method in which the implementation conditions and temperature were varied in the S5) adjusting pH according to the present invention, and the results obtained therefrom.

(1) Experimental Method

The experimental method was carried out based on the method described in Example 2 of the present invention.

In order to prevent gelation of the lung dECM lysate during the pH adjustment process, the pH adjustment process was performed while the tube containing the lysate was kept in ice.

Figure 21:
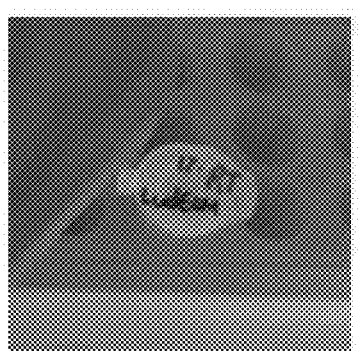
FIG. 21 is a photograph for explaining the process of performing the S5) adjusting pH on ice according to an Example of the present invention.
Figure 21:
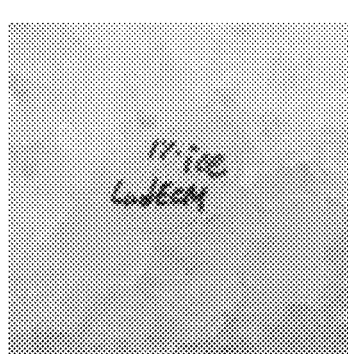

FIG. 21 is a photograph for explaining the process of performing the S5) adjusting pH on ice according to an Example of the present invention. In other words, as shown in FIG. 21, the pH adjustment process was performed in a state in which the container containing the decellularization composition according to the present invention was completely submerged in ice. As a control, the pH adjustment process was performed while the container containing the decellularization composition was placed at room temperature (about 26° C.).

In the pH adjustment process, 10×PBS and 10 N sodium hydroxide (NaOH) were added, and the PBS and NaOH were stored at a refrigeration temperature (1° C. to 10° C.) in advance before use and used in a cold state for pH adjustment.

When the pH was adjusted to be neutral, a dome is made by taking the required amount, and gelation was performed at 37° C. (using an incubator) for 30 minutes (see FIGS. 22, 23 and 24).

Then, the complex modulus (G*) value of the gelated decellularization composition was measured to evaluate the physical properties.

(2) Experimental Results

The physical properties of the lung dECM lysate for each condition of the pH adjustment process are as shown in FIGS. 22 to 25.

Figure 22:
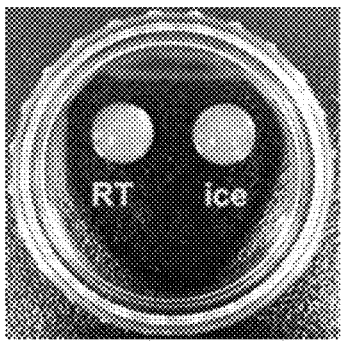
FIGS. 22 to 24 are photographs showing the gelation state of the composition prepared by performing the S5) adjusting pH on ice according to an Example of the present invention.
Figure 22:
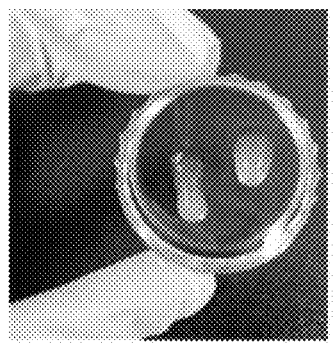
Figure 22:
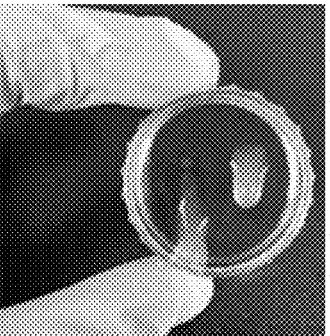
Figure 23:
Figure 24:
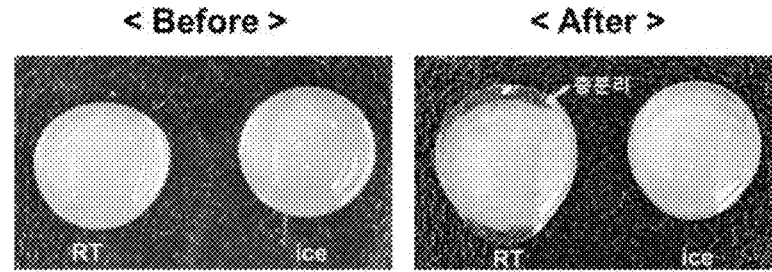
Figure 25:
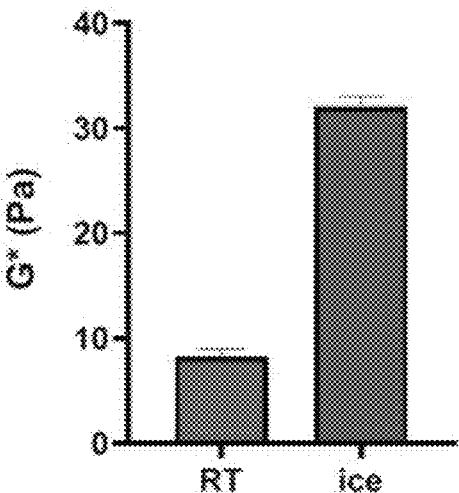
FIG. 25 is a graph showing a modulus value of the composition prepared by performing the S5) adjusting pH on ice according to an Example of the present invention.

FIGS. 22 to 24 are photographs showing the gelation state of the composition for which the S5) adjusting pH was performed on ice according to an Example of the present invention; and FIG. 25 is a graph showing the modulus value of the composition for which the S5) adjusting pH was performed on ice according to an Example of the present invention.

As shown here, when the pH adjustment process was performed on ice as in the present invention, it was found that gelation of the decellularization composition was prevented, and homogeneous hydrogelation was achieved. This facilitates not only the subsequent pipetting and encapsulation but also the organoid culture.

In comparison, when the pH adjustment process was performed at room temperature (RT), a portion of the dECM was partially gelated and aggregated, and as time passed, the separation of the water layer and the decellularization composition occurred, resulting in a non-homogeneous state (see FIGS. 22 and 23).

In addition, after the pH adjustment step, the decellularization composition was gelated at 37° C. for 30 minutes in the same manner as the organoid culture condition, and then the hydrogels made under each pH adjustment condition were observed. The results also showed that the separation of the water layer and the gelated decellularization composition occurred more significantly in the hydrogel of which pH was adjusted at room temperature (RT), confirming that the hydrogel fails to maintain the gel stably and so is incompatible with the organoid culture (see FIG. 24).

According to the results, the decellularization composition of which pH was adjusted at room temperature was difficult to perform pipetting when encapsulating the organoid, and the dome was not maintained but was broken during the culturing of the encapsulated organoid or the culture itself was difficult because the organoid was not encapsulated homogeneously (FIGS. 22, 23 and 24).

In other words, the decellularization composition of which pH was adjusted on ice according to the present invention was able to form a homogeneous gel during the gelation process, but the decellularization composition of which pH was adjusted at room temperature (RT) was partially gelated and aggregated, and the dome was not maintained but was broken, exhibiting low physical properties (complex modulus (G*)) (see FIG. 25).

Figure 26:
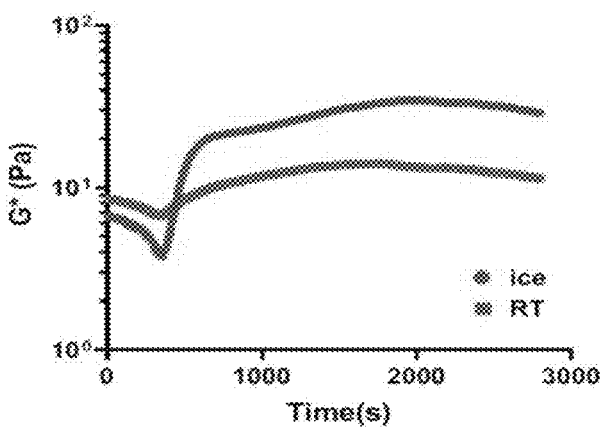
FIG. 26 is a graph showing a gelation kinetic value of the composition prepared by performing the S5) adjusting pH on ice according to an Example of the present invention.

In addition, FIG. 26 is a graph showing the gelation kinetic value of the composition for which the S5) adjusting pH was performed on ice according to an Example of the present invention.

The decellularization composition of which pH was adjusted on ice according to the present invention showed a clear increase in the complex modulus (G*) value during temperature change (4-37° C.), whereas the decellularization composition of which pH was adjusted at room temperature (RT) already showed a high initial G* value and the change of the value was insignificant.

The results suggest that when the pH is adjusted at room temperature (RT), as partial gelation occurs already, a weak and unstable dome can be created due to non-homogeneous gelation. Therefore, the dome may not be maintained during the organoid culture or the culture itself may be difficult (see FIG. 26).

Figure 27:
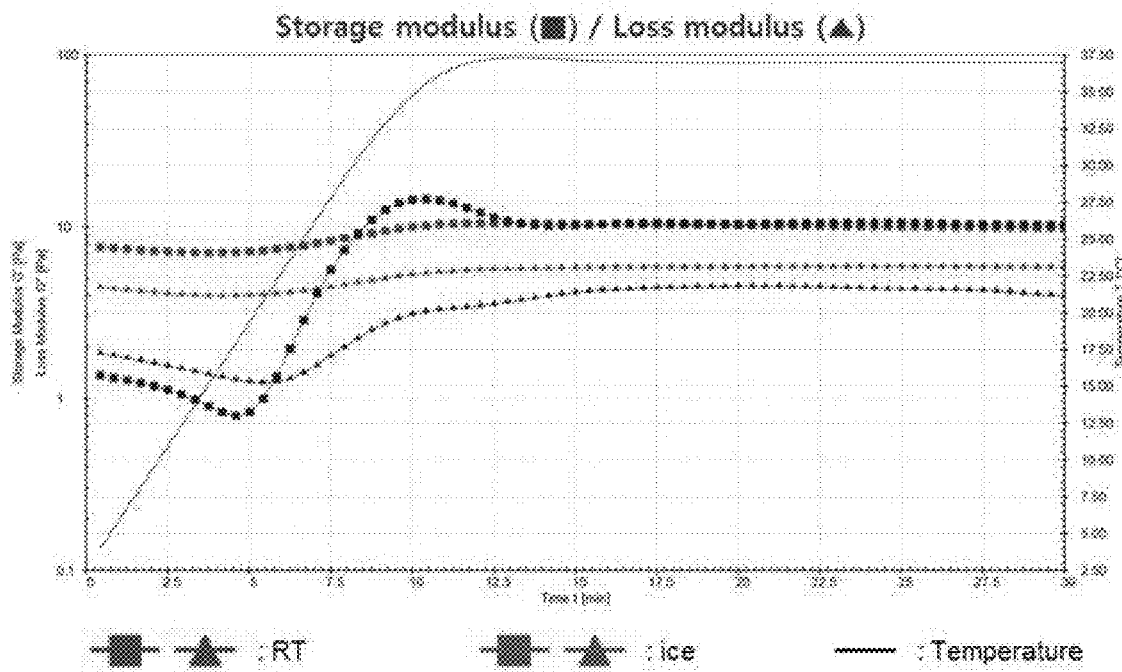
FIG. 27 is a graph showing the change of the physical properties according to an increase of the temperature of the composition prepared by performing the S5) adjusting pH on ice according to an Example of the present invention.

In addition, as a desirable physical property for the organoid culture, the initial state of the dECM should be a sol state (storage modulus < loss modulus) as the temperature changes. However, in the case of the decellularization composition of which pH was adjusted at room temperature, since the initial state of the dECM was already a gel state (storage modulus > loss modulus), not only the pipetting in the encapsulation during the organoid culture but also the encapsulation for the organoid culture could not be carried out, indicating that the decellularization composition was not compatible with the organoid culture (see FIG. 27).

In the above, the applicant has described preferred Examples of the present invention, but these Examples are only one Example that implements the technical principles of the present invention, and any changes or modifications should be construed as being within the scope of the present invention as along as the technical principles of the present invention are implemented.

The invention claimed is:

1. A method for preparing a composition for culturing lung organoids, the method comprising:
  decellularizing lung tissue;
  lyophilizing the decellularized tissue;
  pulverizing the lyophilized tissue;
  lysing the pulverized tissue by adding a proteopeptic enzyme and an acid and stirring at a speed of 330 revolutions for minutes (rpm) to 500 rpm for 72 to 96 hours; and
  adjusting the pH by adding a basic solution to the lysate.

2. The method of claim 1, wherein the lysing the pulverized tissue by adding a proteopeptic enzyme and an acid and stirring is at a speed of 330 rpm for 72 to 96 hours.

3. The method of claim 1, wherein the lysing the pulverized tissue by adding a proteopeptic enzyme and an acid and stirring is at a speed of 330 rpm to 500 rpm for 96 hours.

4. The method of claim 1, wherein the lysing the pulverized tissue by adding a proteopeptic enzyme and an acid and stirring is at a speed of 330 rpm for 96 hours.

\* \* \* \* \*